(12) United States Patent
Bachmann et al.

(10) Patent No.: US 6,713,305 B1
(45) Date of Patent: Mar. 30, 2004

(54) METASTASIS-ASSOCIATED ANTIGEN AND ANTIBODIES THERETO

(75) Inventors: Felix Bachmann, Basel (CH); Max M. Burger, Bottmingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/171,991

(22) PCT Filed: Apr. 18, 1997

(86) PCT No.: PCT/EP97/01963

§ 371 (c)(1),
(2), (4) Date: Oct. 29, 1998

(87) PCT Pub. No.: WO97/41221

PCT Pub. Date: Nov. 6, 1997

Related U.S. Application Data

(60) Provisional application No. 60/016,487, filed on Apr. 29, 1996.

(30) Foreign Application Priority Data

Feb. 28, 1997 (GB) .............................. 9704161

(51) Int. Cl.[7] ........................ G01N 31/00; G01N 33/53; G01N 33/574; G01N 33/567; C12Q 1/00

(52) U.S. Cl. .............................. 436/64; 435/4; 435/7.1; 435/7.2; 435/7.21; 435/7.23; 530/387.1; 530/388.1; 530/388.2; 530/388.8; 530/389.1; 530/389.7

(58) Field of Search .................. 530/387.1, 388.1, 530/388.2, 388.8, 389.1, 389.7; 435/4, 7.1, 7.2, 7.21, 7.23; 436/64

(56) References Cited

FOREIGN PATENT DOCUMENTS

| EP | 0 239 400 | 3/1987 |
| WO | WO 90/07861 | 7/1990 |
| WO | WO9741221 | * 11/1997 |

OTHER PUBLICATIONS

Joswig G. et al., Journal of Cell Science, vol. 98, "Murine cDNAs coding for the centrosomal antigen centrosomin A," pp. 37–43 (1991).
Nagase T. et al., Kazusa DNA Res., Univ. Acad. Press, Inc. Tokyo, vol. 2, "Prediction of the coding sequences of unidentified human genes. IV. The coding sequences of 40 new genes (KIAA0121–KIAA0160) deduced by analysis of cDNA clones from human cell line KG–1," pp. 167–174 (1995).
Nomura N., EMBL Sequence Database, Heidelberg, BRD, Acc. No. D50929, Aug. 1, 1996.
Fisher R., et al., EMBL Sequence Database, Heidelberg, BRD, Acc. No. U14172, Feb. 29. 1996.
Hillier L. et al., EMBL Sequence Database, Heidelberg, BRD, Acc. No. H08975, Jul. 2, 1995.
Hillier L. et al., EMBL Sequence Database, Heidelberg, BRD, Acc. No. N40943, Jan. 27, 1996.
Joswig G. et al., EMBL Sequence Database, Heidelberg BRD, Acc. No. X17373, Mar. 15, 1991.
Joswig G. et al., EMBL Sequence Database, Heidelberg, BRD, Acc. No. X84651, Feb. 13, 1995.
Kanner S.B. et al., Proc. Natl. Acad. Sci. USA, vol. 87, "Monoclonal antibodies to individual tyrosine–phosphorylated protein substrates of oncogene–encoded tyrosine kinases," pp. 3328–3332, May 1990.
Scholler J.K. and Kanner S.B., EMBL Sequence Database, Heidelberg BRD, Acc. No. U58046, Feb. 2, 1997.
Bachmann F. et al., Cancer Res., vol. 57 (5), "Cloning of a Novel Protein Overexpressed in Human Mammary Carcinoma," pp. 988–994 (1997).
Lupas A. et al., Science, vol. 252, "Predicting Coiled Coils from Protein Sequences," pp. 1162–1164 (1991).
Mathias P. et al., Nucleic Acids Research, vol. 17 (15), "Eukaryotic expression vectors for the analysis of mutant proteins," p. 6418 (1989).
Vollmers H.P. and Birchmeier W., Proc. Natl. Acad. Sci. USA, vol. 80, "Monoclonal antibodies inhibit the adhesion of mouse B 16 melanoma cells in vitro and block lung metastasis in vivo," pp. 3729–3733 (1983).
Vollmers H.P. and Birchmeier W., Proc. Natl. Acad. Sci. USA, vol. 80, "Monoclonal antibodies that prevent adhesion of B 16 cells and reduce metastases in mice: Crossreaction with human tumor cells," pp. 6863–6867 (1983). Oct. 1995.*
Lin, M.C. et al. Structure–Function relationships in glucagon: Properties of highly purified Des–His–, Monoiodo–, and [Des–Asn28, thr29](homserine lactone27)–glucagon. Biochemistry, 14(8): 1559–1563, 1975.*
Burgess, W.H. et al. Possible dissociation of the heparin–binding and mitogenic activities of heparin–binding (acidic fibroblast) growth factor–1 from its receptor–binding activities by site–directed mutagenesis of a single lysine residue. J. Cell Biol., Nov. 1990.*
Ensinger, C. et al. Assignment of the p150 subunit of the eukaryotic initiation factor 3A gene (EIF3A) to human chromosome band 10q26 by in situ hybridization. Cyutogenet. Cell Genet. 83: 74–75, 1998.*
Scholler, J.K. et al. The human p167 gene encodes a unique structural protein that contains centrosomin A homology and associates with a multicomponent complex. DNA and Cell Biology 16(4): 515–531, Apr. 1997.*

* cited by examiner

Primary Examiner—Ali R. Salimi
Assistant Examiner—Christopher Yaen
(74) Attorney, Agent, or Firm—Gabriel Lopez; George R. Dohmann; Michael U. Lee

(57) ABSTRACT

There are provided membrane-associated polypeptides having the sequence shown in SEQ ID Nos. 1 and 9. Also provided are immunogenic determinants derived from said polypeptides and antibodies raised thereto. The polypeptides, their derived antigenic determinants and the antibodies are useful for the diagnosis and treatment of metastatic potential in tumors.

3 Claims, 9 Drawing Sheets

FIGURE 1a

```
  1  MPAYFQRPEN ALKRANEFLE VGKKQPALDV LYDVMKSKKH RTWQKIHEPI

51  MLKYLELCVD LRKSHLAKEG LYQYKNICQQ VNIKSLEDVV RAYLKLAEEK

101  TEAAKEESQQ MVLDIEDLDN IQTPESVLLS AVSGEDTQDR TDRLLLTPWV

151  KFLWDHTGSX LDLLRNNSRV ERLYHDIAQQ AFKFCLQYTR KAEFRKLCDN

201  LRIDLSQIQR HHNQSTAINL NNPESQSMHL ETRLVQLDSA ISMELWQEAF

251  KAVEDIHGLF SLSKKPPKPQ LMANYYNKVS TVFWKSGNAL FHASTLHRLY

301  HLSREMRKNL TQEEMQRMST RVLLATLSIP ITPERTDIAR LLDMDGIIVE

351  KQRRLATLLG LQAPPTRIGL INDMVRFSVL QYVVPEVKDL YNWLEVEFNP

401  LKLCERVTKV LNWVREQPEK EPELQQYVPQ LQNNTILRLL QQVAQIYQSI

451  EFSRLTSLVP FVDAFQLERA IVDAARHCDL QVRIDHTSRT LSFGSDLNYA

501  TREDAPVGPH LQSMPSEQIR NQLTAMSSVL AKALEVIRPA HILQEKEEQH

551  QLAVNAYLKN SRKEHQRILA RRQTIEERKE RLESLNIQRE KEELEQREAE

601  LQKYERLKKK GCQEAKEREK ERILQEHEQI KKKTVRERLE QIKKTELGAK

651  AFKDIDIEDL EELDPDFIMA KQVEQLEKEK KELQERLKNQ EKKIDYFERA

701  KRLEEIPLIK SAYEEQRVKD MDLWEQQEEE RITTMQLERE KALEHKNRMS

751  RMLEDRDLFV MRLKAARQSV YEEKLKQFEE RLAEERHSRL EDRKRQRKEE
```

FIGURE 1b

```
801   RKITYYRERK  KKSRGGQRSR  CSKTEKKENV  LREQNAEEEL  REYQERVKKL

851   EEVERKKRQR  ELEIEERERR  REEERRLGDD  PLSRKDSRWG  DRDSEGTWRK

901   GPEADSEWRR  GPPEKEWRRE  TRDDERPHRR  DEDRLRRLGG  DDEERESSLR

951   PDDDRIPRRG  LDDDRGPRRG  PDEDRFSRRG  TDDDRPSWRN  ADDDRPPRRI

1001  GDDDRGSWRH  TDDDRPPRRG  LDDERGSWRT  ADEDRGPRRG  DDDRGPRRG

1051  GADDERSSGG  MLMMIGVPGE  AWMMIGVPGE  GWMMTEDLGG  MLLKIGFPGE

1101  VQMMTEGLGE  IWMMIGFLEG  VMMQDLVLGD  HLSSQVDGER  KKRLEKRVGV

1151  HLENQDHQKN  VNGIETKRRT  EIIKIERRMT  KTLNEIGTER  EMGTGRIRFR

1201  RPRDEGGWRR  GPAEESSSWR  DSSRRDDRDR  EDRRRDRDDR  RDLRDLRDRR

1251  DLRDDRDRRG  PPLRSEREEA  SSWRRTDDRK  DDRTEERDPP  RRVPPPALSR

1301  DRERERREG  EKEKASWRAE  KDRESLRRTK  NETDEDGWTT  VRR
```

FIGURE 2a

```
              1                                                      50
       cenb   ..........  ..........  ..........  ..........  ..........
       cena   ..........  ..........  ..........  ..........  ..........
    p150tot   .MPAYFQRPE  NALKRANEFL  EVGKKQPALD  VLYDVMKSKK  .HRTWQKIHE
     orftab   MAT..FAKPE  NALKRAEELI  TVGQKQEALQ  ALHDLITSRR  .YRAWQKTLE
      egl45   MAPNYFQKPE  AALKRAEELI  QVGKESDALD  TLHDTIKARR  .HKQWTTVHE
   orfyeast   .MAPPPFRPE  NAIKRADELI  SVGEKQAALQ  SLHDFITARR  IRWATPSTVE 51                                                    100
       cenb   ..........  ..........  ..........  ..........  ..........
       cena   ..........  ..........  ..........  ..........  ..........
    p150tot   PIMLKYLELC  VDLRKSHLAK  EGLYQYKNIC  QQV..NIKSL  EDVVRAYLKL
     orftab   RIMFKYVELC  VDMRRGRFAK  DGLIQYRIVC  QQV..NINSL  EEVIKHFMHL
      egl45   QIMIKHMELC  VDLKKQHLAK  DALFQYKALT  QQI..NVKSL  ETVVVHFLKL
   orfyeast   PVVFKFLEIG  VELKKGKLLK  DGLHQYKKLI  QGSTEGLVSV  GAVARKFIDL 101                                                   150
       cenb   ..........  ..........  ..........  ..........  ..........
       cena   ..........  ..........  ..........  ..........  ..........
    p150tot   AEEKTEAAKE  ESQQM..VLD  IEDLDNIQTP  ESVLLSAVSG  EDTQDRTDRL
     orftab   ATERAELARN  QAQALEEALD  VEDLEADKRP  EDLMLSYVSG  EKGKDRSDRE
      egl45   AEQRTEDA..  QKQSIEKVEE  IGDLDQGDVP  ERLLLAVVSG  AAAQDRMDRT
   orfyeast   VESKIASEQT  RADELQKQEI  DDDLEGGVTP  ENLLISVYES  DQSVAGFNDE 151                                                   200
       cenb   ..........  ..........  ..........  ..........  ..........
       cena   ..........  ..........  ..........  ..........  ..........
    p150tot   LLTPWVKFLW  DHTGSXLDLL  RNNSRVERLY  HDIAQQAFKF  CLQYTRKAEF
     orftab   LVTPWFKFLW  ETYRTVLEIL  RNNSRLEALY  AMTAHRAFQF  CKQYKRTTEF
      egl45   VLAPWLRFLW  DSYRNCLELL  RNNAQVEQLY  HTISRHSFTF  CLRYQRRTEF
   orfyeast   AITSWLRFTW  ESYRAVLDLL  RNNALLEITY  SGVVKKTMHF  CLKYQRKNEF
```

FIGURE 2b

```
                201                                                    250
       cenb     ..........  ..........  ..........  ..........  ..........
       cena     ..........  ..........  ..........  ..........  ..........
     p150tot    RKLCDNLRID  LSQIQRHHNQ  STA....INL  NNPESQSMHL  ETRLVQLDSA
      orftab    RRLCEIIRNH  LANLNKYRDQ  RD....RPDL  SAPESLQLYL  DTRFEQLKVA
       egl45    RKLCDLLRMH  LNQIQKHQYA  PNVNSFRVKL  TSPESLGLMQ  DTRLIQLDTA
    orfyeast    KRLAEMLRQH  LDAANYQQSK  SGNNL..VDL  SDADTLQRYL  DQRFQQVDVS 251                                                    300
       cenb     ..........  ..........  ..........  ..........  ..........
       cena     ..........  ..........  ..........  ..........  ..........
     p150tot    ISMELWQEAF  KAVEDIHGLF  SLS....KKP  PKPQLMANYY  NKVSTVFWKS
      orftab    TELGLWQEAF  RSIEDIYGLM  CMV....KKT  PKASLMVVYY  GKLTEIFWMS
       egl45    IQMELWQEAY  KSAEDVHGMM  QLSKDKDKRT  VKPASYVNYY  DKLALVFWKA
    orfyeast    VKLELWHEAY  RSIEDVFHLM  KIS....KRA  PKPSTLANYY  ENLVKVFFVS 301                                                    350
       cenb     ..........  ..........  ..........  ..........  ..........
       cena     ..........  ..........  ..........  ..........  ..........
     p150tot    GNALFHASTL  HRLYHLSREM  RKNLTQEEMQ  RMSTRVLLAT  LSIPITPER.
      orftab    SNHLYHAYAW  LKLFSLQKSF  NKNLSQKDLQ  LIASSVVLAA  LSVPPYDQSY
       egl45    GNSLFHAAAL  LQKFIIYKDM  KKSFTQDEAQ  EQATRVLLAT  LSIPEGSDSP
    orfyeast    GDPLLHTTAW  KKFYKLYSTN  PRA.TEEEFK  TYSSTIFLSA  ISTQLDEIPS 351                                                    400
       cenb     ..........  ..........  ..........  ..........  ..........
       cena     ..........  ..........  ..........  ..........  ..........
     p150tot    TDIARLLDMD  GIIVEKQRRL  ATLLGLQAPP  ........TR  IGLINDMVRF
      orftab    G..ASHLELE  NEKERSLR.V  ANLIGFEVEP  KAENRVALSR  SSLLSELVSK
       egl45    SDLSRNLDIE  DQHVANMRLL  SNLLRLPIAP  ........TK  NGILKEAARI
    orfyeast    IGYDPHL...  ........RM  YRLLNLDAKP  T.......RK  EMLQSIIEDE
```

FIGURE 2c

```
                401                                                           450
      cenb      ..........  ..........  ..........  ..........  ..........
      cena      ..........  ..........  ..........  ..........  ..........
   p150tot      SVLQYVVPEV  KDLYNWLEVE  FNPLKLCERV  TKVLNWVREQ  PEK.......
    orftab      GVMSCVTQEV  KDLYHLLENE  FLPLDLALKV  QPVLSKISKL  GGKLSSVSSV
     eg145      GVPEAAGQTA  KDLYKLLESN  FSPLKVAKDV  QSVLDTVTR.  ..........
  orfyeast      SIYGKVDEEL  KELYDIIEVN  FDVDTVKQQL  ENLLVKLSS.  ..........

451                                                           500
      cenb      ..........  ..........  ..........  ..........  ..........
      cena      ..........  ..........  ..........  ..........  ..........
   p150tot      .EPELQQYVP  QLQNNTILRL  LQQVAQIYQS  IEFSRLTSLV  PF.....VDA
    orftab      PEVQLSQYVP  ALEKLATLRL  LQQVSQVYQT  IQIDNISKMI  PF.....FDF
     eg145      ..PDHLQYVE  SLQAVAAVKA  LKQVSVIYEA  ISWERIRKII  PF.....YSD
  orfyeast      .KTYFSQYIA  PLRDVIMRRV  FVAASQKFTT  VSQSELYKLA  TLPAPLDLSA 501                                                           550
      cenb      ..........  ..........  ..........  ..........  ..........
      cena      ..........  ..........  ..........  ..........  ..........
   p150tot      FQLERAIVDA  ARHCDLQVRI  DHTSRTLSFG  .......SDL  NYATREDAPV
    orftab      TVIEKISVDA  VRRNFLAIKV  DHMKG.....  ......LSSL  VNRVLRRKD.
     eg145      LALERLVVEA  SKHRIVKAQL  DHRADCVRFG  SSD.ATLAGG  VDECDNNEGF
  orfyeast      WDIEKSLLQA  AVEDYVSITI  DHESAKVTFA  KDPFDIFAST  ASKEVSEEEN 551                                                           600
      cenb      ......MPSE  QIRNQLTAMS  SVLAKAIEVI  RPAHILQEKE  EQHQL.....
      cena      ......MPSE  QIRNQLTAMS  SVLAKAIEVI  RPAHILQEKE  EQHQL.....
   p150tot      GPHLQSMPSE  QIRNQLTAMS  SVLAKALEVI  RPAHILQEKE  EQHQL.....
    orftab      SGIICLFLAE  SLSKARTMIY  PPAKKAAKLG  EALSNLAEIV  EK........
     eg145      TGDDTQLGVE  GVRNHLEAMY  TRLRGLVEGL  DAEKRRKEIL  KKIEG.....
  orfyeast      TEPEVQEEKE  ETDEALGPQE  TEDGEEKEEE  SDPVIIRNSY  IHNKLLELSN
```

FIGURE 2d

```
              601                                                        650
     cenb     ...AVNAYLK  NSRKEHQRIL  ARRQTIEERK  ERLESLN...  IQREKEELEQ
     cena     ...AVNAYLK  NSRKEHQRIL  ARRQTIEERK  ERLESLN...  IQREKEELEQ
  p150tot     ...AVNAYLK  NSRKEHQRIL  ARRQTIEERK  ERLESLN...  IQREKEELEQ
   orftab     ..........  ....EHKRLL  ARKSIIEKRK  EEQERLL...  LEMERVEETK
    egl45     ...QVTSYEK  NRPTEIERIH  RRKKMLENYK  ENWERVK...  AEKTAAAATE
 orfyeast     VLHDVDSFNN  ASYMEKVRI.  ARETLIKKNK  DDLEKISKIV  DERVKRSQEQ 651                                                        700
     cenb     REAELQKV..  .....RKAEE  ERLPRGKGAR  EGT.NPSRTR  ANQEEN..CS
     cena     REAELQKV..  .....RKAEE  ERLPRGKGAR  EGT.NPSRTR  ANQEEN..CS
  p150tot     REAELQKY..  ..........  ERLKK.KGCQ  EAK.EREKER  ILQEHEQIKK
   orftab     RRDVQKMT..  .....EEAEQ  KRI.....AA  ....EYEQRR  NQRILKEIED
    egl45     QAKREEAA..  .....RAEEM  KRL.....DE  QNK.ESERKR  KQAEQDEIQK
 orfyeast     KQKHMEHAAL  HAEQDAEVRQ  QRILEEKAAI  EAKLEEEAHR  RLIEKKKREF 701                                                        750
     cenb     GAVRADQED.  ...RLGAKAF  KDIDIEDLEE  LDPDFIMAKQ  VEQLEKEKKD
     cena     GAVRADQED.  ...RLGAKAF  KDIDIEDLEE  LDPDFIMAKQ  VEQLEKEKKD
  p150tot     KTVRERLEQI  KKTELGAKAF  KDIDIEDLEE  LDPDFIMAKQ  VEQLEKEKKE
   orftab     RELEEAQ.AL  LHEAEKRSKR  KKKPVLEGEK  MTKKVIMELA  LNEQLRERQE
    egl45     KIKQDQLYKM  QQNAIYQEII  KEKGLEQFRD  MDPEQVLREQ  RERLDKERAE
 orfyeast     EAIKEREITK  MITEVNAKGH  VYIDPNEAKS  LDLDTIKQVI  IAEVSKNKSE 751                                                        800
     cenb     YQERLKNQEK  KIDYFERAKR  LEEIPLIKSA  YEEHRVKDMD  LWEQQEEERI
     cena     YQERLKNQEK  KIDYFERAKR  LEEIPLIKSA  YEEHRVKDMD  LWEQQEEERI
  p150tot     LQERLKNQEK  KIDYFERAKR  LEEIPLIKSA  YEEQRVKDMD  LWEQQEEERI
   orftab     MEKKLLKFAK  SMDHLERAKR  EEAAPLIESA  FKQRLAEEAA  LHEREQQQEI
    egl45     TQRRLQQQEK  NFDHHVRALH  LEELNERRAV  MNMRLSEAPK  LHDLYEEARI
 orfyeast     LESRMEYAMK  KLDHTERALR  KVELPLLQKE  VDKLQETDTA  NYEAMKKKIV
```

FIGURE 2e

```
              801                                                    850
     cenb   TTMQLEREKA LEHKNRMSRM LEDRDLFVMR LKVARQSVYE EKLKQFEERL
     cena   TTMQLEREKA LEHKNRMSRM LEDRDLFVMR LKVARQSVYE EKLKQFEERL
  p150tot   TTMQLEREKA LEHKNRMSRM LEDRDLFVMR LKAARQSVYE EKLKQFEERL
   orftab   ELSRQRHAGD LEEKRRLARM LENKRILQEK VVSSREAEFT RMKRERQERI
    egl45   AKEIAAHDSH VKLWGMWDQV RDATFDWVES VKIDNQETLE KKLSDWQAKL
 orfyeast   DAAKAEYEAR MADRKNLVMV YDDYLKFKEH VSGTKESELA AIRNQKKAEL 851                                                    900
     cenb   AEERHSRLED RKRQRKEERK ITYYREKEEE EQRRAEEQML KEREERERAE
     cena   AEESIVA*.. .......... .......... .......... ..........
  p150tot   AEERHSRLED RKRQRKEERK ITYYRERKKK SRGGQRSRCS KTEKKENVLR
   orftab   SQIIQSRKQE REARRKM... ..IFFLRSEE ERQKRLQEEE ......EARK
    egl45   EAVRNNRLAE RAEDRKKKRK EDAIQAKIAE ERKKREEEER ARLQVIEGQR
 orfyeast   EAAKKARIEE VRKRRYEE.. .......... .......... ..........

901                                                    950
     cenb   RAKREEELRE YQERVKKLEE VERKKRQREL EIEERERRRE EERRLGDDPL
     cena   .......... .......... .......... .......... ..........
  p150tot   EQNAEEELRE YQERVKKLEE VERKKRQREL EIEERERRRE EERRLGDDPL
   orftab   REEAERRKKE EAE....... ....RQAKLD EIAEKQRRRM LELEEKEKRE
    egl45   RQHNDGRGRR EMENSVAMQD NDWRRNPPRE SLPPRETRPM RDGPTREPRE
 orfyeast   .........A IARRKEEIAN AERQKRAQEL AEATRKQREI EEA.......

951                                                   1000
     cenb   SRKDSRWGDR DSEGTWRKGP EADSEWRRGP PEKEWRRETR DDERPHRRDE
     cena   .......... .......... .......... .......... ..........
  p150tot   SRKDSRWGDR DSEGTWRKGP EADSEWRRGP PEKEWRRETR DDERPHRRDE
   orftab   .......... .......... .......... .......... REEILRKSTA
    egl45   FRGDRDREPR EPFREVPSSK ADTDNSWRSS AQPTRKPDDR RSDEFRRNDD
 orfyeast   ..AAKKSTPY SFRAGNREPP STPSTLPKAT VSPDKAKLDM IAQKQREMEE
```

FIGURE 2f

```
             1001                                                  1050
    cenb   DRLRRLGGDD EERESSLRPD DDRIPRRG*. .......... ..........
    cena   .......... .......... .......... .......... ..........
 p150tot   DRLRRLGGDD EERESSLRPD DDRIPRRGLD DDRGPRRGPD EDRFSRRGTD
  orftab   V......... .LPKPAEPPT LGRPAELGGA APIPAAAATA P......TPG
    eg145  VRRNDDVRRN DPPRPASKAD TGDKWERGVK PVVSPPKTDA PSVSEPKSEG
 orfyeast  AIEQRLAGRT AGGSSPATPA TPATPATPTP SSGPKKMTMA EKLRAKRLAK 1051                                                  1100
    cenb   .......... .......... .......... .......... ..........
    cena   .......... .......... .......... .......... ..........
 p150tot   DDRPSWRNAD DDRPPRRIGD DDRGSWRHTD DDRPPRRGLD DERGSWRTAD
  orftab   PGKYVPKHLR TKMDGAGQAP PPE..TDKWG GGSKPDDRPS WRDE.RKPPS
    eg145  PKRFVPPHLR NRQGGGGAGG SEEQSAPARS GNSNVTSPPD RAQGLRGPPP
 orfyeast  GGR....... .......... .......... .......... ..........

1101                                                  1150
    cenb   .......... .......... .......... .......... ..........
    cena   .......... .......... .......... .......... ..........
 p150tot   EDRGPRRGMD DDRGPRRGGA DDERSSGGML MMIGVPGEAW MMIGVPGEGW
  orftab   FGSGSRTSWP ASRR...... .......... .......... ..........
    eg145  TGRNSLPRRD GPPPRSNNTG NTGNADSGSW RK........ ..........
 orfyeast  .......... .......... .......... .......... ..........

1151                                                  1200
    cenb   .......... .......... .......... .......... ..........
    cena   .......... .......... .......... .......... ..........
 p150tot   MMTEDLGGML LKIGFPGEVQ MMTEGLGEIW MMIGFLEGVM MQDLVLGDHL
  orftab   .......... .......... .......... .......... ..........
    eg145  .......... .......... .......... .......... ..........
 orfyeast  .......... .......... .......... .......... ..........
```

FIGURE 2g

```
                 1201                                                    1250
        cenb     ..........  ..........  ..........  ..........  ..........
        cena     ..........  ..........  ..........  ..........  ..........
     p150tot     SSQVDGERKK  RLEKRVGVHL  ENQDHQKNVN  GIETKRRTEI  IKIERRMTKT
      orftab     ..........  ..........  ..........  ..........  ..........
        egl45    ..........  ..........  ..........  ..........  ..........
     orfyeast    ..........  ..........  ..........  ..........  ..........

1251                                                    1300
        cenb     ..........  ..........  ..........  ..........  ..........
        cena     ..........  ..........  ..........  ..........  ..........
     p150tot     LNEIGTEREM  GTGRIRFRRP  RDEGGWRRGP  AEESSSWRDS  SRRDDRDRED
      orftab     ..........  ..........  ..........  ..........  ..........
        egl45    ..........  ..........  ..........  ..........  ..........
     orfyeast    ..........  ..........  ..........  ..........  ..........

1301                                                    1350
        cenb     ..........  ..........  ..........  ..........  ..........
        cena     ..........  ..........  ..........  ..........  ..........
     p150tot     RRRDRDDRRD  LRDLRDRRDL  RDDRDRRGPP  LRSEREEASS  WRRTDDRKDD
      orftab     ..........  ..........  ..........  ..........  ..........
        egl45    ..........  ..........  ..........  ..........  ..........
     orfyeast    ..........  ..........  ..........  ..........  ..........

1351                                                    1400
        cenb     ..........  ..........  ..........  ..........  ..........
        cena     ..........  ..........  ..........  ..........  ..........
     p150tot     RTEERDPPRR  VPPPALSRDR  ERERREGEK   EKASWRAEKD  RESLRRTKNE
      orftab     ..........  ..........  ..........  ..........  ..........
        egl45    ..........  ..........  ..........  ..........  ..........
     orfyeast    ..........  ..........  ..........  ..........  ..........

1401       1411
        cenb     ........... .
        cena     ........... .
     p150tot     TDEDGWTTVR  R
      orftab     ........... .
        egl45    ........... .
     orfyeast    ........... .
```

METASTASIS-ASSOCIATED ANTIGEN AND ANTIBODIES THERETO

This application is the National Stage filing under 35 U.S.C. 371 of PCT International Application ser. No. PCT/EP97/01963 (designating the United States), filed Apr. 18, 1997, which claims priority under 35 U.S.C. 119(e) from U.S. Ser. No. 60/016,487, filed Apr. 29, 1996 now abandoned.

The present invention relates to a novel antigen which is closely associated with metastatic behaviour of tumour cells in vitro and in vivo, as well as to antibodies recognising said antigen and uses thereof in diagnosis and treatment of malignancies.

Metastasis is a multi-stage process by which tumour cells leave the site of a primary tumour, enter blood and lymph vessels, migrate to distant parts of the body and form novel foci of tumour growth. In keeping with the apparently complex nature of metastasis, experimental data suggest that no one factor is exclusively responsible for the determination of metastatic potential. Rather, a cascade of events, each of which incrementally increases the liability of a tumour to metastasis, leads to metastasis and tumour spread. Each of the events of the metastatic cascade is not believed to play a role of identical importance in each metastatic situation. A given metastatic cell is likely to possess some less developed metastatic properties, but still possess high metastatic potential because other properties are highly pronounced.

For this reason, a reliable marker for metastatic potential is difficult to determine. There are indications, however, that the cell surface is closely involved with many aspects of the metastatic cascade. The detachment of tumour cells, migration through tissues and final attachment to form a new focus of growth are events which all involve the behaviour of the cell surface.

It is known to attempt to raise antibodies directed to antigens preferentially expressed by tumour cells which show metastatic potential. For example, Vollmers and Birchmeier, (1983) PNAS 80, 3739–3733 & 6863–6867, demonstrated that certain antibodies raised to mouse melanoma cell line surface protein were able to inhibit cell adhesion and block metastasis. The antibodies appeared to target antigens of between 40 and 50 kDa.

By raising antisera to membrane associated proteins and assessing cross-reactivity with transformed cells, we have now been able to identify novel 150 kDa cell-surface proteins which correlate extremely closely with metastatic potential both in vitro and in vivo.

SUMMARY OF THE INVENTION

According to the present invention, we provide membrane-associated polypeptides having the sequence shown in SEQ ID NOS. 2 and 9, respectively. Also provided are immunogenic determinants derived from said polypeptides and antibodies raised thereto. The polypeptides, their derived antigenic determinants and the antibodies are useful for the diagnosis and treatment of metastatic potential in tumours.

BRIEF DESCRIPTION OF THE FIGURES

FIG. 1 shows the deduced amino acid sequence of the metastasis-related antigen p150 isolated from mouse. The sequence data derived by amino acid microsequencing is underlined.

FIG. 2 shows a sequence homology comparison between p150 from mouse and related sequences.

DETAILED DESCRIPTION OF THE INVENTION

By raising monoclonal antibodies to membrane fractions derived from human placenta and subsequently screening the antibodies for cell surface staining in transformed versus non-transformed cells, an antibody which identifies an antigen preferentially expressed on transformed cells can be identified. This antigen, referred to herein as p150 from mouse, has an apparent molecular weight on SDS-PAGE of ca. 150 kDa and the sequence shown in SEQ ID No. 2. The human homologue is represented in SEQ ID No. 9.

The antigens are expressed in tumours, tumour cell lines and primary cells derived from tumours, and appear at much lower levels in normal human tissue. The levels of expression of the antigens are not consistent between tumours and cell lines derived therefrom, including primary cell lines. However, within each separate system, we have determined that the antigens closely correlate with metastatic potential. The level of expression of the antigens appears to be dependent on the differentiation state of the tumour cell. Thus, relatively undifferentiated tumour cells, which have a high metastatic potential, express relatively high levels of p150, while more differentiated cells express a lower amount of these antigens. Tumour tissue derived from actual metastases appears to express the most elevated levels of p150.

The present invention includes the p150 proteins both from mouse and human and all derivatives thereof which are useful for diagnosing the metastatic potential of a tumour. Preferably, unless otherwise indicated or implied, such derivatives are encompassed by the term "p150". The high degree of correlation of p150 with metastatic potential makes the antigens useful for determining the correct treatment to be used, as it is known that a high metastatic potential correlates with a poor prognosis. Accordingly, the derivatives of p150 comprised in the invention include all those which retain characteristics of p150 which allow them to be identified in diagnostic assays. The preferred characteristic retained by the p150 derivatives of the invention is a common antigenic determinant shared with p150.

"Common antigenic determinant" means that the derivative in question at least one antigenic function of p150. Antigenic functions includes possession of an epitope or antigenic site that is capable of cross-reacting with antibodies raised against a naturally occurring or denatured p150 polypeptide or fragment thereof. Thus p150 as provided by the present invention includes splice variants encoded by mRNA generated by alternative splicing of a primary transcript, amino acid mutants, glycosylation variants and other covalent derivatives of p150 which retain the physiological and/or physical properties of p150. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of p150 found with a particular species, preferably a mammal. Such a variant may be encoded by a related gene of the same gene family, by an allelic variant of a particular gene, or represent an alternative splicing variant of the p150 gene.

Derivatives which retain common antigenic determinants can be fragments of p150. Fragments of p150 comprise individual domains thereof, as well as smaller polypeptides derived from the domains. Preferably, smaller polypeptides derived from p150 according to the invention define a single epitope which is characteristic of p150. Fragments may in theory be almost any size, as long as they retain one characteristic of p150. Preferably, fragments will be between 5 and 500 amino acids in length. Longer fragments are regarded as truncations of the full-length p150 and generally encompassed by the term "p150".

Derivatives of p150 also comprise mutants thereof, which may contain amino acid deletions, additions or substitutions, subject to the requirement to maintain at least one feature characteristic of p150. Thus, conservative amino acid substitutions may be made substantially without altering the nature of p150, as may truncations from the 5' or 3' ends. Deletions and substitutions may moreover be made to the fragments of p150 comprised by the invention. p150 mutants may be produced from a DNA encoding p150 which has been subjected to in vitro mutagenesis resulting e.g. in an addition, exchange and/or deletion of one or more amino acids. For example, substitutional, deletional or insertional variants of p150 can be prepared by recombinant methods and screened for immuno-crossreactivity with the native forms of p150.

The fragments, mutants and other derivative of p150 preferably retain substantial homology with p150. As used herein, "homology" means that the two entities share sufficient characteristics for the skilled person to determine that they are similar in origin and function. Preferably, homology is used to refer to sequence identity. Thus, the derivatives of p150 preferably retain substantial sequence identity with the sequences of SEQ ID Nos. 2 and 9, respectively.

"Substantial homology", where homology indicates sequence identity, means more than 50% sequence identity, preferably more than 75% sequence identity and most preferably a sequence identity of 90% or more.

Preferably, the proteins or derivatives thereof of the invention are provided in isolated form. "Isolated" means that the respective protein or derivative thereof has been identified and is free of one or more components of its natural environment. Isolated p150 includes p150 in a recombinant cell culture. P150 present in an organism expressing a recombinant p150 gene, whether the p150 protein is "isolated" or otherwise, is included within the scope of the present invention.

The polypeptides according to the invention are closely associated with the metastatic process in tumour cells. Accordingly, the invention provides a composition comprising a polypeptide according to the invention or an antagonist thereto for use as a medicament in the treatment or diagnosis of tumours.

According to a further aspect of the present invention, there are provided nucleic acids encoding p150. In addition to being useful for the production of recombinant p150 protein, these nucleic acids are also useful as probes, thus readily enabling those skilled in the art to identify and/or isolate nucleic acid encoding p150. The nucleic acid may be unlabelled or labelled with a detectable moiety. Furthermore, nucleic acids according to the invention are useful e.g. in a method determining the presence of p150-specific nucleic acid, said method comprising hybridising the DNA (or RNA) encoding (or complementary to) p150 to test sample nucleic acid and determining the presence of p150. In another aspect, the invention provides nucleic acid sequences that are complementary to, or hybridise under stringent conditions to, a nucleic acid sequence encoding p150.

The invention also provides a method for amplifying a nucleic acid test sample comprising priming a nucleic acid polymerase (chain) reaction with nucleic acid (DNA or RNA) encoding (or complementary to) p150.

In still another aspect of the invention, the nucleic acid is DNA and further comprises a replicable vector comprising the nucleic acid encoding p150 operably linked to control sequences recognised by a host transformed by the vector. Furthermore the invention provides host cells transformed with such a vector and a method of using a nucleic acid encoding p150 to effect the production of p150, comprising expressing p150 nucleic acid in a culture of the transformed host cells and, if desired, recovering p150 from the host cell culture.

Furthermore, the present invention relates to isolated p150 proteins and derivatives thereof encoded by the above-described nucleic acids.

Isolated p150 nucleic acid includes a nucleic acid that is free from at least one contaminant nucleic acid with which it is ordinarily associated in the natural source of p150 nucleic acid or in crude nucleic acid preparations, such as DNA libraries and the like. Isolated nucleic acid thus is present in other than in the form or setting in which it is found in nature. However, isolated p150 encoding nucleic acid includes p150 nucleic acid in ordinarily p150-expressing cells where the nucleic acid is in a chromosomal location different from that of natural cells or is otherwise flanked by a different DNA sequence than that found in nature.

In accordance with the present invention, there are provided isolated nucleic acids, e.g. DNAs or RNAs, encoding p150, particularly mammalian p150, e.g. human p150, or fragments thereof. In particular, the invention provides DNA molecules encoding p150, or a fragment thereof. By definition, such a DNA comprises a coding single stranded DNA, a double stranded DNA of said coding DNA and complementary DNA thereto, or this complementary (single stranded) DNA itself. Exemplary nucleic acids encoding p150 are represented in SEQ ID Nos. 1 and 8.

The preferred sequences encoding p150 are those having substantially the same nucleotide sequence as the coding sequences in SEQ ID Nos. 1 and 8, with the nucleic acids having the same sequence as the coding sequences in SEQ ID Nos. 1 and 8 being most preferred. As used herein, nucleotide sequences which are substantially the same share at least about 90% identity. However, in the case of splice variants having e.g. an additional exon sequence homology may be lower.

The nucleic acids of the invention, whether used as probes or otherwise, are preferably substantially homologous to the sequences of p150 as shown in SEQ ID Nos. 1 and 8. The terms "substantially" and "homologous" are used as hereinbefore defined with reference to the p150 polypeptide(s).

Preferably, nucleic acids according to the invention are fragments of the p150-encoding sequences, or derivatives thereof as hereinbefore defined in relation to polypeptides. Fragments of the nucleic acid sequences of a few nucleotides in length, preferably 5 to 150 nucleotides in length, are especially useful as probes.

Exemplary nucleic acids can alternatively be characterised as those nucleotide sequences which encode a p150 protein and hybridise to the DNA sequences set forth SEQ ID Nos. 1 and 8, respectively, or a selected fragment of said DNA sequences. Preferred are such sequences encoding p150 which hybridise under high-stringency conditions to the sequences of SEQ ID Nos. 1 and 8, respectively.

Stringency of hybridisation refers to conditions under which polynucleic acids hybrids are stable. Such conditions are evident to those of ordinary skill in the field. As known to those of skill in the art, the stability of hybrids is reflected in the melting temperature ($T_m$) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na$^+$ at 65–68° C. High stringency conditions can be provided, for example, by hybridisation in an aqueous solution containing 6×SSC, 5×Denhardt's, 1% SDS (sodium dodecyl sulphate), 0.1 Na$^+$ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess p150 and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding p150 is to use PCR technology as described e.g. in section 14 of Sambrook et al., 1989. This method requires the use of oligonucleotide probes that will hybridise to p150 nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to p150; oligonucleotides of about 20 to 80 bases in length that encode known or suspected p150 cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding p150 may be isolated by screening suitable cDNA or genomic libraries under suitable hybridisation conditions with a probe, i.e. a nucleic acid disclosed herein including oligonucleotides derivable from the sequences set forth in SEQ ID Nos. 1 and 8. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases set forth in SEQ ID Nos. 1 and 8, respectively. The nucleic acid sequences selected as probes should be of sufficient length and sufficiently unambiguous so that false positive results are minimised. The nucleotide sequences are usually based on conserved or highly homologous nucleotide sequences or regions of p150. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating a$^{32P}$ dATP with the Klenow fragment of DNA polymerase in a random priming reaction, as is well known in the art. Oligonucleotides are usually end-labelled with g$^{32P}$-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire p150-encoding sequence or a suitable oligonucleotide based on a portion of said DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete p150 (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous p150, genetic screening may be carried out using the nucleotide sequences of the invention as hybridisation probes. Such probes can e.g. be used to screen specific tissues and body fluids like e.g. blood, urine, spinal-fluid, ascites and serum. Also, based on the nucleic acid sequences provided herein antisense-type therapeutic agents may be designed.

It is envisaged that the nucleic acids of the invention can be readily modified by nucleotide substitution, nucleotide deletion, nucleotide insertion or inversion of a nucleotide stretch, and any combination thereof. Such mutants can be used e.g. to produce a p150 mutant that has an amino acid sequence differing from the p150 sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

The cDNA or genomic DNA encoding native or mutant p150 can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequences that enable the vector to replicate in one or more selected host cells. Typically in cloning vectors, these sequences are those which enable the vector to replicate independently of the host chromosomal DNA, and include origins of replication or autonomously replicating sequences. Such sequences are well known for a variety of bacteria, yeast and viruses. The origin of replication from the plasmid pBR322 is suitable for most Gram-negative bacteria, the 2m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another organism for expression. For example, a vector is cloned in $E.$ $coli$ and then the same vector is transfected into yeast or mammalian cells even though it is not capable of replicating independently of the host cell chromosome. DNA may also be replicated by insertion into the host genome. However, the recovery of genomic DNA encoding p150 is more complex than that of exogenously replicated vector because restriction enzyme digestion is required to excise p150 DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in $E.$ $coli,$ an $E.$ $coli$ genetic marker and an $E.$ $coli$ origin of replication are advantageously included. These can be obtained from $E.$ $coli$ plasmids, such as pBR322, Bluescript® vector or a pUC plasmid, e.g. pUC18 or pUC19, which contain both $E.$ $coli$ replication origin and $E.$ $coli$ genetic marker conferring resistance to antibiotics, such as ampicillin.

Suitable selectable markers for mammalian cells are those that enable the identification of cells competent to take up p150 nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes p150. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to p150 nucleic acid. Such a promoter may be inducible or constitutive. The promoters are operably linked to DNA encoding p150 by removing the promoter from the source DNA by restriction enzyme digestion and inserting the isolated promoter sequence into the vector. Both the native p150 promoter sequence and many heterologous promoters may be used to direct amplification and/or expression of p150 DNA.

Promoters suitable for use with prokaryotic hosts include, for example, the b-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding p150, using linkers or adaptors to supply any required restriction sites. Promoters for use in bacterial systems will also generally contain a Shine-Delgarno sequence operably linked to the DNA encoding p150.

Moreover, the p150 genes according to the invention preferably include a secretion sequence in order to facilitate secretion of the corresponding polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

p150 gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with p150 sequence, provided such promoters are compatible with the host cell systems.

Transcription of a DNA encoding p150 by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to p150 DNA, but is preferably located at a site 5' from the promoter.

Advantageously, a eukaryotic expression vector encoding p150 may comprise a locus control region (LCR). LCRs are capable of directing high-level integration site independent expression of transgenes integrated into host cell chromatin, which is of importance especially where the p150 gene is to be expressed in the context of a permanently-transfected eukaryotic cell line in which chromosomal integration of the vector has occurred, in vectors designed for gene therapy applications or in transgenic animals.

Suitable eukaryotic host cells for expression of p150 include yeast, fungi, insect, plant, animal, human, or nucleated cells from other multicellular organisms will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNAs encoding p150.

An expression vector includes any vector capable of expressing p150 nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding p150 may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding p150 in mammalian cells. Transient expression usually involves the use of an expression vector that is able to replicate efficiently in a host cell, such that the host cell accumulates many copies of the expression vector, and, in turn, synthesises high levels of p150. For the purposes of the present invention, transient expression systems are useful e.g. for identifying p150 mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing p150 expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing p150. Suitable prokaryotes include eubacteria, such as Gram-negative or Gram-positive organisms, such as *E. coli*, e.g. *E. coli* K-12 strains, DH5a and HB101, or Bacilli. Further hosts suitable for p150 encoding vectors include eukaryotic microbes such as filamentous fungi or yeast, e.g. *Saccharomyces cerevisiae*. Higher eukaryotic cells include insect and vertebrate cells, particularly mammalian cells. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of p150-encoding nucleic acid to form p150. The precise amounts of DNA encoding p150 may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby p150 encoded by the DNA is expressed. The composition of suitable media is known to those in the art, so that they can be readily prepared. Suitable culturing media are also commercially available.

While the DNAs provided herein may be expressed in any suitable host cell, e.g. those referred to above, preferred for expression of DNA encoding functional p150 are eukaryotic expression systems such as baculovirus-based systems and, particularly, mammalian expression systems, including commercially available systems and other systems known to those of skill in the art.

In preferred embodiments, p150 encoding DNA is ligated into a vector, and introduced into suitable host cells to produce transformed cell lines that express p150. The resulting cell lines can then be produced in quantity for reproducible qualitative and/or quantitative analysis of the effect(s) of potential drugs affecting p150 function. Thus p150 expressing cells may be employed for the identification of compounds, particularly small antagonising molecules interfering with p150 function are useful. An alternative to achieve an antagonistic effect is to rely on over-expression of antisense p150 RNA. Thus host cells expressing p150 are useful for drug screening and it is a further object of the present invention to provide a method for identifying compounds which modulate and preferable reduce the activity of p150, said method comprising exposing cells containing heterologous DNA encoding p150, wherein said cells produce functional p150, to at least one compound or signal whose ability to modulate the activity of said p150 is sought to be determined, and thereafter monitoring said cells for changes caused by said modulation. Such an assay enables the identification of agonists, antagonists and allosteric modulators of p150.

Cell-based screening assays can be designed e.g. by constructing cell lines in which the expression of a reporter protein, i.e. an easily assayable protein, such as b galactosidase, chloramphenicol acetyltransferase (CAT) or luciferase, is dependent on p150. Such an assay enables the detection of compounds that directly modulate p150 function, e.g. compounds that antagonise p150, or compounds that inhibit other cellular functions required for the activity of p150. An in vitro assay for p150 requires that it may be produced in large amounts in a functional form using recombinant DNA methods. An assay is then designed to measure a functional property of the p150.

It has been found that p150 is expressed mostly in cells of high metastatic potential. Thus the present invention also provides a method to exogenously affect p150 dependent processes occurring in such cells. Recombinant p150 producing host cells, e.g. mammalian cells, can be contacted with a test compound, and the modulating effect(s) thereof can then be evaluated by comparing the p150-mediated response in the presence and absence of test compound, or relating the p150-mediated response of test cells, or control cells (i.e., cells that do not express p150), to the presence of the compound.

As used herein, a compound or signal that modulates the activity of p150 refers to a compound that alters the activity of p150 in such a way that the activity of p150 is different in the presence of the compound or signal (as compared to the absence of said compound or signal).

The invention also provides a transgenic non-human mammal which has been modified to modulate the expression of endogenous p150. Preferably, the transgenic non-human mammal is a transgenic mouse. For example, therefore, a transgenic mouse may be designed in which p150 production is greatly reduced or eliminated Alternatively, the transgenic mouse of the invention may express elevated levels of p150, or may be subject to regulation of p150 expression in a developmentally or tissue-specific manner, or via control by exogenous agents. Study of such an animal provides insights into the importance of p150 in vivo.

Moreover, since the polypeptides according to the invention are closely associated with the metastatic process in tumour cells, the invention provides a composition comprising a nucleic acid encoding a polypeptide according to the invention or an antagonist thereto for use as a medicament in the treatment or diagnosis of tumours.

In a preferred embodiment, there is provided a transcription unit encoding a polypeptide according to the invention or an antagonist thereto for use in a method of treatment of a tumour or other condition, for example a condition involving aberrant p150 gene expression, by gene therapy techniques. The transcription unit provided according to the present aspect of the invention comprises regulatable control regions which include a promoter, together with one or more enhancers and/or LCRs. The transcription unit may be delivered to the subject by any suitable means, including viral vectors, especially retroviral vectors, adeno- and adeno associated viral vectors, non-viral delivery systems, including liposomal and antibody targeted delivery systems, and direct uptake of naked DNA. The target tissue is advantageously a tumour tissue.

In accordance with yet another embodiment of the present invention, there are provided antibodies specifically recognising and binding to p150. For example, such antibodies may be generated against the p150 having the amino acid sequences set forth in SEQ ID Nos. 2 and 9, respectively. Alternatively, p150 or p150 fragments (which may also be synthesised by in vitro methods) are fused (by recombinant expression or an in vitro peptidyl bond) to an immunogenic polypeptide and this fusion polypeptide, in turn, is used to raise antibodies against a p150 epitope.

Anti-p150 antibodies are recovered from the serum of immunised animals. Alternatively, monoclonal antibodies are prepared from cells in vitro or from in vivo immunised animals in conventional manner. Preferred antibodies identified by routine screening specifically identify p150 on tumour cells with a high metastatic potential.

The antibodies of the invention are useful for studying p150 tissue localisation, screening of an expression library to identify nucleic acids encoding p150 or the structure of functional domains, as well as for the purification of p150, and the like. Preferably, however, they are useful in the diagnosis and treatment of tumours and especially tumour metastasis.

Antibodies according to the invention may be whole antibodies of natural classes, such as IgE and IgM antibodies, but are preferably IgG antibodies. Moreover, the invention includes antibody fragments, such as Fab, F(ab')$_2$, Fv and ScFv. Small fragments, such Fv and ScFv, possess advantageous properties for diagnostic and therapeutic applications on account of their small size and consequent superior tissue distribution.

The antibodies according to the invention are especially indicated for the diagnosis and therapy of cancer. Accordingly, they may be altered antibodies comprising an effector protein such as a toxin or a label. Especially preferred are labels which allow the imaging of the distribution of the antibody in a tumour in viva. Such labels may be radioactive labels or radioopaque labels, such as metal particles, which are readily visualisable within the body of a patient. Moreover, the may be fluorescent labels or other labels which are visualisable on tissue samples removed from patients.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [see international patent application WO 90/07861 (Protein Design Labs)].

Antibodies according to the invention may be obtained from animal serum, or, in the case of monoclonal antibodies or fragments thereof, produced in cell culture. Preferably, monoclonal antibodies according to the invention are antibody 6G7 (DSM 2256) and antibody 6G10 (DSM 2257). Recombinant DNA technology may be used to produce the antibodies according to established procedure, in bacterial or preferable in mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antibodies, preferentially by immunofluorescent staining of cells expressing p150, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno)-affinity chromatography, e.g. affinity chromatography with p150 protein or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed to p150, characterised in that a suitable mammal, for example a Balb/c mouse, is immunised with purified p150 protein, an antigenic carrier containing purified p150 or with cells bearing p150, antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with cells bearing p150 are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells of human tumour origin which express p150 containing a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant DNAs comprising an insert coding for a heavy chain variable domain and/or for a light chain variable domain of antibodies directed to the extracellular domain of p150 as described hereinbefore. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed p150 can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant DNAs comprising an insert coding for a heavy chain murine variable domain of an antibody directed p150 fused to a human constant domain g, for example g1, g2, g3 or g4, preferably g1 or g4. Likewise the invention concerns recombinant DNAs comprising an insert coding for a light chain murine variable domain of an antibody directed to p150 fused to a human constant domain k or l, preferably k.

In another embodiment the invention pertains to recombinant DNAs coding for a recombinant antibody wherein the heavy chain variable domain and the light chain variable domain are linked by way of a DNA insert coding for a spacer group, optionally comprising a signal sequence facilitating the processing of the antibody in the host cell and/or a DNA coding for a peptide facilitating the purification of the antibody and/or a DNA coding for a cleavage site and/or a DNA coding for a peptide spacer and/or a DNA coding for an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Antibodies and antibody fragments according to the invention are useful in the diagnosis and therapy of tumours. Accordingly, the invention provides a composition for the therapy or diagnosis of tumours comprising an antibody according to the invention.

In the case of a diagnostic composition, the antibody is preferably provided together with means for detecting the antibody, which may be enzymatic, fluorescent, radioisotopic or other means. These means can e.g. be used to screen specific tissues and body fluids like e.g. blood, serum, ascites, spinal-fluid and urine. The antibody and the detection means may be provided for simultaneous, simultaneous separate or sequential use, in a diagnostic kit intended for the diagnosis of tumour conditions.

The invention further provides a method for determining the metastatic potential of a tumour cell, comprising assessing the level of p150 expression in said cell, a higher level of p150 expression being indicative of a lower state of differentiation and consequently a higher metastatic potential.

Moreover, the invention provides a method for the therapy of tumours comprising administering to a patient a therapeutically effective dose of an antibody, a polypeptide or a nucleic acid according to the invention.

The invention is further described, for the purposes of illustration only, in the following examples.

EXAMPLE 1
Metastasis-specific antibody

Due to the interest in the molecular components playing a role in the metastatic cascade monoclonal antibodies (Mabs) are raised against fractions containing membrane proteins derived from human placenta in order to identify such molecules possibly involved in this complex event.

Membrane-associated proteins are isolated from human placental tissue. The rationale for the selection of placental tissue is that since the trophoblast invades surrounding tissue, it is likely that invasion-associated proteins will be expressed therein.

200 g fresh human placenta is used as a starting material. The placenta is cut into small pieces and then washed several times in ice cold PBS in order to remove blood. The small pieces are transferred into a beaker containing 200 ml lysis buffer (100 mM Octyl-beta-D-glucoside, 1 mM PMSF, 5 mg/ml Leupeptin and 1 mM $Mn^{2+}$ dissolved in PBS), homogenised with a Warren blender, stirred for 4 h at 4° C. and then once again homogenised with a Polytron. Solid matter is then removed by centrifugation at 25000 g for 60 minutes.

The supernatant is applied to a preequilibrated 10 ml column charged with Sepharose® conjugated with the hexapeptide GRGDSP. The column is then extensively washed with lysis buffer. Bound material is eluted in lysis buffer containing 10 mM EDTA. 1 ml eluate fractions are analysed by SDS-PAGE under reducing conditions.

Balb/c mice are then used for raising Mabs against putative RGD-binding proteins. Each animal receives about 50–100 mg of partially purified membrane proteins derived from the Sepharose®-GRGDSP column, plus 0.5 ml Freunds Adjuvants injected ip. As booster applications, the animals twice receive 50–100 mg of protein plus 0.5 ml Freunds incomplete Adjuvants every 3–4 weeks. Finally, 2 days before the fusion of the splenocytes with the myeloma cells (PAI cells), the animals receive another 20–30 mg of protein intravenously. The resulting Mabs are screened for cell surface staining and expression levels of the newly defined antigens in transformed versus non transformed cells. Comparison is made between 3T3 cells in a non-transformed state, and 3T3 cells transformed with src or ras, as well as CEF68 cells grown at permissive or non-permissive temperatures.

Cell surface staining is analysed by immunofluorescence, as follows. Cells are grown on glass coverslips or on glass slides, washed in PBS or in DME and fixed for 30 min. in formaldehyde 3.7% in PBS or in DME at room temperature (20° C.). Cells are then permeabilised in 0.5% TX-100 (in PBS or DME) for 1–3 min at room temperature. Subsequently, cells are washed 3–4 times in PBS or DME at room temperature. Liquid is drained off and 0.03 ml of a first antibody raised against the membrane-associated protein fractions diluted in DME/10% FCS is added. The cells are incubated for 60 minutes at 37° C. in a humid incubator.

After incubation, the cells are washed 3–4 times in PBS or DME at room temperature. 0.03 ml of a second, anti-mouse antibody labelled with FITC or TRITC diluted in DME /10% FCS is added, and the cells incubated for 60 minutes at 37° C. in a humid incubator. Subsequently, they are washed 3–4 times in PBS or DME and once in water. They are then embedded in an appropriate mounting medium and stored in the dark. Fluorescence can then be assessed by viewing the embedded cells using suitable fluorescence microscopy equipment.

An interesting MAb, H11VII, is selected and further tested in the B16 F1/F10 mouse melanoma system. For this purpose melanoma cells are incubated with the MAb prior to tail vein injection into mice. After 3 weeks the animals are sacrificed and the lung colonies counted. A 80–85% inhibition of the lung colonisation ability can be observed.

In order to reconfirm the results obtained with the original MAb (H11VII) a new set of Mabs against mouse p150 is raised. The outcome of the in vivo lung colonisation assay performed with the new anti-p150 Mabs is shown in Table 1.

TABLE 1

| B16 F1 cells | | | | |
|---|---|---|---|---|
| treatment | number of lung colonies | mean | std | % inhibition |
| control | 25,16,2,1,14,20,25,24 | 16 | 10 | |
| H11VII | 1,0,5,9,0,4,0,0,5,9 | 3 | 4 | 80 |

| B16 F10 cells | | | | |
|---|---|---|---|---|
| treatment | number of lung colonies | mean | std | % inhibition |
| untreated | 36,45,23,20,52,64, >300(64), >300(64) | 46 | 8 | |
| control | 27,22,38,22,20,28,37,64, 93,>300(93) | 44 | 29 | |
| H11VII | 0,0,0,1,3,4,10,11,12,16 | 6 | 6 | 85 |

| B16 F1 cells H11VII induced | | | | |
|---|---|---|---|---|
| treatment | number of lung colonies | mean | std | fold induc. |
| control | 2,6,5,5,13,0,3,1,2,35 | 4 | 4 | |
| H11VII ind 0h | 28,97,92,37,61,7,43,17, 5,47 | 43 | 32 | 10 |
| H11VII ind 40h | 41,45,47,74,21,26,51,127, 101,131 | 66 | 40 | 16 |

| B16 F1 cells | | | | |
|---|---|---|---|---|
| treatment | number of lung colonies | mean | std | % inhibition |
| 4H9 | 0,3,>50,>50,22,>50,20 | ? | ? | promotion? |
| 6G7 | 1,9,4,9,2,1,4,3,8,0 | 4 | 3 | 80 |
| H11VII | 11,1,13,11,0,7,16 | 8 | 5 | 50 |
| control | 22,33,24,7,19,30,4,34 | 22 | 11 | |
| 1B10 | 25,1,13,13,0,7,8,16,10 | 10 | 8 | 50 |
| 6G10 | 9,6,3,4,7,2,2,7,23,0 | 6 | 6 | 70 |

A general problem by using antibodies in an in vivo system is the possible stimulation of the host immune system. Especially the cytotoxic as well as the natural killer activities towards cells tagged with antibodies can be influenced. Due to the fact that peripheral cellular blood components do not express p150 in detectable amounts, it is possible to reduce the influence of the host immune system by changing the treatment. Instead of incubation of the cancer cells with Mabs prior to injection we pretreat the host animals 24 hrs before they received F1 cells. The results of this experiment, in which the original MAb (H11VII) as well as a new MAb raised against mouse p150 (6G7) are used, are outlined in Table 2.

TABLE 2

| B16 F1 cells injected into pretreated animals | | | | |
|---|---|---|---|---|
| pretreatment | number of lung colonies | mean | std | % inhibition |
| control | 1,4,13,31,40,44,63,>99(63), >99(63),>99(63) | 39 | 25 | n/a |
| H11VII | 1,1,5,7,10,15,17,25,41 | 14 | 13 | 65 |
| 6G7 | 0,1,2,5,6,11,19,20,22 | 10 | 9 | 75 |

Mice are pretreated with the monoclonal antibodies for 24 hours before injection of B16 cells. 0.5 mg of antibody is injected i.p. Antibodies are prepared by precipitation in 28 g/100 ml $(NH_4)_2SO_4$ and ConA chromatography.

EXAMPLE 2
Metastasis-specific antigen

Using western blotting according to standard protocols, antibody H11VII is seen to recognise bands on SDS-PAGE migrating at approximately 28, 35, 70 and 150 KDa. The bands are purified from the gel and rabbit polyclonal antisera raised thereto. The antiserum raised against the 28 KDa band cross-reacts with the 150 KDa band on western blots.

The antigen recognised by MAb H11VII can be identified as a 150 kDa membrane associated protein (p150). P150 is expressed in B16F1 cells in large amounts. Therefore, these cells are used as starting material for the purification of p150.

A crude membrane fraction is isolated from B16F1 cells by centrifugation at 100,000 g and lysis in 1%NP40, 2 mM Tris-HCl pH 7.5, containing PMSF and aprotinin protease inhibitors. The supernatant is loaded on a Sepharose® column, run off, transferred to a Sepharose® S column, again run off, and separated by reducing SDS-PAGE on a 5% gel. The 150 KDa band is electrocuted.

EXAMPLE 3
Analysis of p150 and cDNA cloning

P150 is microsequenced by digestion with trypsin, V8 and Lys-C followed by sequencing using Edman degradation on an Applied Biosystems sequencer. An oligonucleotide deduced from the sequence used to probe a mouse melanoma B16F1 library.

Sequencing the clones picked out of the B16F1 mouse melanoma c-DNA library identifies an ORF of 3.6 kb encoding the 142 kDa carboxy terminal part of p150. The missing 5' part was obtained by applying race technique using a kit from Clontech. Taking all the sequence information together, we can establish an ORF of 4.03 kb encoding a polypeptide of 1343 aa. This ORF, referred to as p150 is shown in SEQ ID No. 1. The deduced protein sequence is shown in SEQ ID No. 2 and FIG. 1. The peptide sequences obtained from protein microsequencing are underlined in FIG. 1. The cDNA and derived amino acid sequences of the human homologue, also referred to as p150 are shown in SEQ ID Nos. 8 and 9, respectively.

Striking homologies are found between p150 and two mouse proteins called centrosomin A (280 amino acids from the sequence shown in SEQ ID No. 3) and B (430 amino acids from the sequence shown in SEQ ID No. 4) respectively. These two proteins are most likely splice variants. They are found to be associated with centrosomes. Unfortunately no functional studies have been carried out on centrosomins, but, due to the cellular localisation, they are thought to take part in the organisation of the spindle apparatus and therefore could be candidates for possible tubulin binding.

Sequence alignment between p150, centrosomin A and centrosomin B shows that the centrosomins share close homology with p150 throughout their lengths, but p150 extends both 5' and 3' of both centrosomins. A sequence comparison is given in FIG. 2.

Another 3 ORFs showing significant homologies to p150 exist in the Swiss Prot databank. A yeast ORF (YBR079; SEQ ID No. 5) showing 51% similarity and 29% identity, a tobacco ORF (NTPNL35; SEQ ID No. 6) with 59% similarity and 37% identity and an ORF found in nematode C.elegans (EGL-45; SEQ ID No. 7) showing 56% similarity and 36% identity. Unfortunately functional data are available only for EGL-45; the two other ORFs are of unknown function. Mutational studies performed on EGL-45 suggest an involvement of this protein in the regulatory steps of the hermaphrodite specific neuronal differentiation. Expression of EGL-45 is found in most cells of the worm. Null mutants give rise to a sterile or even a lethal phenotype.

All four sequences show a common overall organisation: namely a stretch of 300 aa at the amino terminus with significant identities between 30–45%, followed by a stretch of about 200aa of little homology which is followed by a highly charged stretch of about 400aa predicted to form coiled-coil domains (according to Lupas et al., Science 252, 1162, 1991).

The sequence alignments of 6 proteins described hereinabove (including the centrosomins) are shown in FIG. 2.

EXAMPLE 4
Metastasis-specific expression of p150

It is reasoned that p150 on B16F1/F10 cells must be expressed on the cell surface, otherwise it would not be possible to influence the metastatic cascade by applying Mabs to the cell surface. In order to verify the localisation of p150, FACS analysis is carried out as follows:

Starting with a confluent 6 cm tissue culture dish with B16 F1 or F10 cells (in DME-medium), antibody (dilution 1/10–1/100) is added to adherent cells or detached cells (EDTA, PBS w/o $Ca^{2+}/Mg^{2+}$, wash once in PBS/1% BSA, spin down and add the antibody).

Cells are incubated either on the tissue culture plate (at 20 or 37° C.) or in an Eppendorf tube for 1–2 h. Subsequently, cells are washed with PBS/1% BSA on the plate and detached, or washed by spinning down in the Eppendorf tube and adding PBS/1% BSA. The washing step is repeated 3–4 times.

Cells which were labelled on the plate are then taken up in 1 ml PBS/1% BSA.

A second antibody conjugated with FITC or TRITC is added to the cells in PBS/1% BSA and incubated for 1 h at 20° C. while slowly shaking. The cells are washed 2–3 times with PBS/1% BSA. A FACscan may then be carried out according to standard protocols.

FACS analysis demonstrates that P150 is clearly expressed at the cell surface of B16 F1 mouse melanoma cells. The labelling pattern as well as the intensity of the staining is independent of the fact whether the cells were labelled in suspension or they were attached to tissue culture dishes.

Results are confirmed by cell surface biotinylation on living F1 cells, as follows:

A confluent 15 cm dish of B16 F1 or HeLa cells is washed 3–4 times with cold PBS. 10 ml PBS containing 0.05 ml Biotinamidocaproate-N-Hydroxysuccimide Ester (Sigma B 2643), which was dissolved in DMSO at 100mg/ml, is then added and the cells incubated for 40–60 minutes in the cold room (4° C.).

The cells are then washed 2–3 times with cold PBS and lysed in cold lysis buffer (see p150 purification) for 30 minutes on ice. Undissolved material is spun down at 13000 g for 10 minutes and the cleared cell lysate incubated with Avidin Agarose beads for 30 minutes on a shaker in the cold room.

The Avidin Agarose beads are washed with lysis buffer 3–4 times, once with cold $ddH_2O$ and boiled in SDS-PAGE sample buffer. SDS-PAGE is run and western blotting carried out according to standard protocols.

B16 F1 cells are seen to express p150 on the cell surface as determined by the above cell surface biotinylation method. However only a very small proportion of total cellular p150 is exposed at the cell surface. This seems to be involved in cell-cell and/or in cell-extracellular matrix interactions as already indicated by the results obtained from the in vivo colonisation experiments. Contrary to this finding in B16 cells, in HeLa cells no cell surface biotinylation of p150 could be observed.

According to its amino acid sequence, p150 contains a hydrophobic stretch of 70 aa (1050–1120), which could serve as a transmembrane domain. However, most of the cellular p150 is found in the cytoplasmic compartment associated with endogenous membranes.

On HeLa cells, in contrary to the B16F1 cells, p150 could not be detected on the cell surface by biotinylation technique. Therefore, it might be possible, that the distribution of p150 depends on the cell type and on its status.

B16 cells show a strong transformed phenotype; e.g. they do not spread out very well in cell culture. As a consequence, the cytoskeletal elements are not as well separated as in cells which show a more spread out phenotype. Therefore we chose HeLa cells for our localisation studies. Using confocal microscopy, a strong perinuclear staining is observed, while throughout the cytoplasm staining is associated with vescicular structures. In cells undergoing mitosis, staining is observed to be associated with the midbody, in a pattern similar to that of tubulin.

Assessed by western blotting according to standard procedures, p150 is normally expressed in several mouse organs. We find a high expression level in pancreas, as well as liver, although signal in liver might be artefact due to high protein concentration in that region, and a medium level in brain, thymus, and testis. Low expression of p150 occurs in lung, spleen and kidney. P150 expression in testis could reflect the fact that there we can find a lot of undifferentiated, proliferating cells. In testis, p150 and b-tubulin codistribute on structures resembling sperm tails.

In order to analyse the connection between transformation and p150 expression, we analyse various cell types in different states of transformation using western blotting and find that a positive correlation between the state of transformation and the expression level of p150 can be observed. Thus, we observe higher levels of p150 in 3T3 cells transformed with ras than in non-transformed cells, and much higher levels in 3T3 cells transformed with v-src. CEF cells transformed with a temperature sensitive transforming gene product, NY68, show higher levels of p150 expression at the permissive (37° C.) than the non-permissive (41° C.) temperature.

When the expression of p150 assessed by western blotting is correlated to differentiation state, an inverse relationship between the grade of differentiation and the expression level of p150 is observed in all cell lines so far investigated, including ES cells differentiated according to standard procedures, stably differentiated F9 cells and B16F1 cells treated with retinoic acid (0.01 and 0.1 M).

The expression of p150 correlates inversely with malignancy in different B16 variants. The two most malignant variants, F10 and LS9, have a lower level of p150 expression than F1 cells. This seems to contradict the relationship between transformation state and p150 expression levels. However, it is known that in the B16 system the metastatic ability in most cases correlates directly with differentiation state. Thus, in B16 cells, the more differentiated cells are more malignant. This is in contradistinction to what is found in other model systems and in clinics where greater malignancy and poor prognosis correlates inversely with differentiation state.

In order to examine the expression of p150 in other systems, several human tumour cell lines are tested for p150 expression. Some breast cancer cell lines (HBL 100, BT 20, T47D, SKBR3, MB231 and MB453), a liver cancer cell line (Hep G2) as well as a ovarian cancer cell line (SKO V3) are investigated. The p150 levels are different in these lines, but p150 appears to be universally present.

EXAMPLE 5

Expression of p150 in human tumours

Methods

Tumor and normal tissue samples

From 22 fresh mastectomy specimen, cancer tissue and non-cancerous normal tissue is chosen macroscopically by an experienced pathologist for transfer to the laboratory. The tissue arrives in the laboratory about 5 hours after mastectomy at latest, is frozen and stored at −80° C. Corresponding cancer and normal tissue are fixed in 10% buffered formalin and embedded in paraffin. 5 micron sections are cut for hematoxylin/eosin staining. For immunohistochemistry the 5 micron sections are mounted on cementit (Merz und Benteli SA, Niederwangen, Switzerland) covered super frost slides. Presence of invasive cancer and of normal tissue is confirmed by histology in each case.

Preparation of tissue extracts

Frozen human tumor and normal tissue is cut into small pieces, suspended in STE buffer (0.1 M NaCl, 0.01 M Tris-HCl pH 7.6, 1 mM EDTA) with protease inhibitors aprotinin 2 μg/ml, leupeptin 1 μg/ml and 1 mM PMSF and homogenized with a Polytron homogenizer. The homogenates are centrifuged at 1000 g for 15 minutes and the supernatants are mixed with one volume of 2×sample buffer consisting of 0.1 M Tris-HCl pH 6.8, 4% SDS and 20% glycerol. This mixture is incubated for 30 minutes at 56° C. and recentrifuged at 15,000 g for 10 minutes. The protein concentration of the supernatants is determined with a BCA protein assay kit (Pierce, Rockford, Ill.).

Preparation of NP-40 extracts of cell lines

Cells are washed twice with PBS and lysed in ice-cold lysis buffer (0.01 mM Tris-HCl pH 7.5, 0.5% Nonidet P-40 and 1 mM PMSF) in the dish for 30 minutes at 4° C. The lysed cells are centrifuged at 15,000 g at 4° C. The supernatants are mixed with sample buffer as described above. The samples are heated for 2 minutes at 95° C. and the protein concentrations determined.

Immunoblotting

Extracts of cells or surgical specimens containing 20 or 40 μg of protein are subjected to electrophoresis in the presence of 0.1% SDS in 5% SDS-PAGE minigels. After electrophoresis, the proteins are transferred electrophoretically at 1 mA per $cm^2$ for 90 minutes onto a PVDF membrane. The membranes are blocked in blocking solution (0.1 M Tris-HCl pH 7.4, 0.1 M $MgCl_2$, 0.5% Tween 20, 1% Triton X-100, 1% BSA, 5% FCS) for 30 minutes at room temperature (RT), decorated with a chicken Ab against p150 (Sophie 1:2000) or with Mab 6G10 (supernatant 1:20) overnight at 4° C., washed with blocking solution and then incubated for 1 hour at RT with a goat anti-chicken peroxidase-coupled second antibody (1:2000, Southern Biotechnology Ass. Inc., Birmingham, Ala.) or rabbit anti-mouse and swine anti-rabbit (both peroxidase-coupled, Dako Diagnostics AG, Zug, Switzerland) at dilutions of 1:2000. Then the membranes are washed with blocking solution, PBS and water and the protein-antibody complexes are visualized by ECL (Amersham International, UK) according to the manufacturer's protocol. Quantification of the Western blots are done by using a $^{125}$Iodine-labeled second antibody (Amersham International, UK). The blots are scanned with a Phosphorimager unit (Molecular Dynamics, Sunnyvale, Calif.) and the relative amounts of p150 are determined by measuring the radioactivity present in the appropriate bands.

Immunohistochemistry

Representative tissue blocks of normal and carcinoma tissue are taken from three cases for immunohistological examination. The 5 micron paraffin sections are deparaffinized, rehydrated and washed twice in Tris-NaCl buffer (30 mM Tris (pH 7.5), 0.9% NaCl). Internal peroxidases are blocked with blocking solution (25 mM β-D-glucose, 25 mM sodium azide and 0.6 units/ml glucose oxidase (Sigma, Switzerland) in Tris-NaCl buffer) for 1 hour at 37° C. After washes in Tris-NaCl buffer, the sections are heated in 500 ml citrate buffer (0.1 mM, pH 6.0) in the microwave oven operated at 750 W for 10 minutes. The sections are allowed to cool down and washed again in Tris-NaCl buffer before blocking with 1% BSA in Tris-NaCl buffer for 15 minutes. The chicken antibody against p150 (Sophie 1/1000) is applied for 60 minutes at RT in the same buffer, whereas the Mab 6G7, the monospecific rabbit anti-$NH_2$ terminal peptide (225 amino acids) antibody and the Mab against Ki-67 (MIB1, Dianova GmbH, Germany) are incubated with the sections overnight at 6° C. Subsequently the sections are washed twice, incubated with second antibodies (goat anti-chicken, goat anti-mouse or goat anti-rabbit; all peroxidase coupled, diluted 1:2000, Southern Biotechnology Ass. Inc., Birmingham, Ala.) for half an hour, rinsed with Tris-NaCl-buffer and incubated with the peroxidase substrate 3'-3'-diaminobenzidine (Sigma, Switzerland) 2% in 50 mM Tris pH 7.6 for 5 to 10 minutes at RT. The paraffin sections are counterstained with stabilized hematoxylin (Shandon, Astmoore, GB), dehydrated, mounted in Depex (BDH, Gurr, UK) and photographed.

A. Screening of 22 mammary carcinoma

Expression of p150 in human mammary tumors

Based on the fact that transformation and dedifferentiation are main features of cancer cells primary human tumors are screened for p150 expression using the panel of antibodies developed in the early stage of these studies.

The mean age of our 22 patients with primary breast cancer when operated was 64 years (range 37–90 y) and the mean tumor size was 48 mm (range 20–140 mm). 55% of the tumors were poorly differentiated (GIII according to the Elston and Ellis grading system (12)) while 14% were well differentiated. The predominant histological type (91%) was ductal invasive, the others were lobular invasive tumors. Metastasis to axillary lymph nodes was detected in 59%, in 27% the lymph nodes showed no metastasis and from all other patients no lymph nodes were available. In 21 of the 22 patients Western blotting have revealed significantly higher p150 expression in tumors than in the normal tissue counterparts of the same patients. With patient #14139 we have been able to investigate lymphnode metastasis; p150 expression in this context is even higher than in the primary carcinoma. One case (#10594) displayed an aberrant result. This patient, however, was the only one who had received preoperative chemotherapy and did not show any p150 overexpression in the cancer tissue.

Immunohistochemistry

A distinct pattern of p150 expression is observed in breast cancer tissue versus the control tissue. Invasive and in situ ductal cancer react equally positive. Necrotic tissue is found to be negative for p150 expression.

Normal non proliferating tissue shows faint focal cytoplasmic staining of luminal epithelial cells as do myoepithelial cells. A few nuclei in proliferating epithelial cells also present positive staining. Stromal tissue is negative for p150 in all cases.

Proliferative and precancerous alterations in breast tissue such as epitheliosis, apocrine metaplasia and adenosis show staining for p150. No correlation between Ki-67 staining and p150 expression in normal breast tissue is observed.

B. Screening of additional 31 mammary carcinoma

The mean age of the 31 patients with primary breast cancer when operated was 61 years (range 36–85 years) and the mean tumor size was 28 mm (range 9–90 mm). Fifty-five percent of the cancers were poorly differentiated (GIII according to the Elston and Ellis grading system), 32% were moderately differentiated and 13% were benign. The predominant histological type (67%) was ductal invasive, the others were lobular invasive (16%), fibroadenomas (10%), one squamous cell carcinoma, one a mucinous carcinoma and one was a papilloma.

Metastasis to lymphnode was detected in 42%, in 29% no lymph nodes were involved and in 29% of the patients lymph nodes were not available. Thirty of 31 patients show significantly higher p150 expression in tumors than in normal tissue counterparts in Western blot analysis.

One patient (#18976) shows no p150 expression neither in the normal breast tissue nor in the carcinoma. By histology this tumor is determined to be a rare squamous cell carcinoma of the breast. Interestingly, squamous cell carcinomas of the cervix show almost a loss of p150 expression as soon as the tumor starts to invade. Therefore, it is suggested, that the behavior in p150 expression is strongly dependent on the histological type and origin of the particular tumor.

Remarkably, p150 expression in the benign fibroadenomas and papilloma is much lower than in malignant mammary carcinoma.

C. Screening of cervical cancer

Extensive studies have been carried out on squamous cell carcinoma of the cervix. Specimens of 165 patients have been investigated by immunohistochemistry. According to histological grading they have been divided into 3 groups containing 77 cases with precancerous lesions, 68 cases with invasive tumors and 20 healthy controls. The precancerous lesions significantly present the highest level of p150 expression whereas invasive stages show expression levels comparable to controls. Furthermore 120 month survival is significantly increased ($p<0.01$) in those patients who show highest expression levels of p150.

In contrast to mammary carcinoma, malignancy in cervical squamous cell carcinoma inversely correlates with p150 expression levels. Apparently, the behavior of neoplastic tissue in terms of p150 expression strongly depends on the histological origin. Therefore, it is not a general issue for p150, that expression levels increase with enhanced proliferative ability. Thus it appears that p150 can be used both as a dedifferentiation and as a proliferation marker.

D. Screening of colon cancer

Nine cases of colon cancer are investigated by Western blot analysis. p150 is clearly upregulated in all nine cases in comparison with the control tissue. An additional band of about 120 kD which is considered to be a degradation product, appears exclusively in the carcinoma. This additional band is not recognized by an antibody against the $NH_2$-terminal peptide of p150. This implies that in colon carcinoma the amino-terminal part of p150 might be specifically degraded by high protease activity.

Immunohistochemistry, which is done on 120 cases including the 9 cases presented in Western blot analysis, clearly reconfirms our findings. Furthermore, the results suggest that p150 plays a role in the dedifferentiation process in colorectal carcinoma.

E. Screening of lung and thyroid cancer

Several cases of lung and thyroide cancer are investigated as well. The data suggest an upregulation of p150 in these malignancies too.

F. Screening of oesophagal cancer

Several cases of oesophagal cancer are investigated as well. From 70 cases 30 are screened by Western blot analysis and 40 by immunohistochemistry. All tissue samples screened with either method show positive results.

Deposit Data:

Antibodies according to the invention have been deposited in accordance with the Budapest Treaty at the Deutsche Sammlung von Mikroorganismen und Zellkulturen, Maschenroder Weg 1b, D-3300 Braunschweig, Germany, under the following accession numbers:

| Antibody | Accession No. | Deposit Date |
| --- | --- | --- |
| 6G7 | DSM 2256 | Apr. 11, 1996 |
| 6G10 | DSM 2257 | Apr. 11, 1996 |

What is claimed is:

1. A method of detecting cells of metastatic potential comprising the steps of:
   (a) contacting an antibody of accession no. DSM2256 or DSM2257 with a cell or tissue sample, said antibody being capable of specifically recognizing an epitope of a polypeptide comprising an amino acid sequence encoded by a nucleotide sequence according to SEQ ID No:1 or SEQ ID No:8, and
   (b) detecting binding of said antibody to said cell or tissue sample.

2. An isolated monoclonal antibody obtained from a hybridoma deposited under accession nos. DSM2256 or DSM2257.

3. A method of identifying cells with metastatic potential comprising the steps of:
   (i) providing an antibody of accession nos. DSM2256 or DSM2257 capable of specifically recognizing an epitope of a cell-membrane associated polypeptide encoded by a nucleic acid sequence according to SEQ ID No: 1 or SEQ ID No: 8,
   (ii) incubating said antibody with cell of interest, and
   (iii) detecting binding of said antibody to said cells, wherein the antibody binding indicates said cells have metastatic potenial.

* * * * *

SEQUENCE LISTING

<160> NUMBER OF SEQ ID NOS: 9

<210> SEQ ID NO 1
<211> LENGTH: 5137
<212> TYPE: DNA
<213> ORGANISM: Mus sp.
<220> FEATURE:
<221> NAME/KEY: CDS
<222> LOCATION: (128)..(4156)

<400> SEQUENCE: 1

```
gccggctggg cgcgggcatc tgctggcgag gcgcgtggaa gctcgcgcta gttccctcc      60 gccttctctc ccggtccagg ccactaggga gttcgctgac gccgggtgaa ctgagcgtac    120 cgtcaag atg ccg gcc tat ttc cag agg ccg gaa aat gcc ctc aag cgc    169
        Met Pro Ala Tyr Phe Gln Arg Pro Glu Asn Ala Leu Lys Arg
        1               5                   10 gcc aac gaa ttt ctt gag gtt ggc aaa aag cag cct gcc ctg gat gtt    217
Ala Asn Glu Phe Leu Glu Val Gly Lys Lys Gln Pro Ala Leu Asp Val
 15                  20                  25                  30 ctt tat gat gta atg aaa agt aag aag cac aga aca tgg cag aag ata    265
Leu Tyr Asp Val Met Lys Ser Lys Lys His Arg Thr Trp Gln Lys Ile
                 35                  40                  45 cat gag cca att atg ctg aaa tac ttg gaa ctg tgt gtg gat ctt cgt    313
His Glu Pro Ile Met Leu Lys Tyr Leu Glu Leu Cys Val Asp Leu Arg
             50                  55                  60 aag agc cac ttg gct aag gaa ggg tta tat caa tat aag aac ata tgc    361
Lys Ser His Leu Ala Lys Glu Gly Leu Tyr Gln Tyr Lys Asn Ile Cys
         65                  70                  75 caa cag gta aac att aaa tct tta gaa gat gtt gtt agg gca tat ttg    409
Gln Gln Val Asn Ile Lys Ser Leu Glu Asp Val Val Arg Ala Tyr Leu
     80                  85                  90 aaa tta gca gag gaa aaa aca gaa gct gct aaa gaa gag tcc caa caa    457
Lys Leu Ala Glu Glu Lys Thr Glu Ala Ala Lys Glu Glu Ser Gln Gln
 95                 100                 105                 110 atg gtg tta gat ata gaa gat ctg gat aat att cag act cct gag agt    505
Met Val Leu Asp Ile Glu Asp Leu Asp Asn Ile Gln Thr Pro Glu Ser
                115                 120                 125 gtt ctc tta agt gca gta agt ggg gaa gat act cag gat cgt act gac    553
Val Leu Leu Ser Ala Val Ser Gly Glu Asp Thr Gln Asp Arg Thr Asp
            130                 135                 140 aga ttg cta ctg act ccc tgg gtc aag ttc ctg tgg gat cat aca ggc    601
Arg Leu Leu Leu Thr Pro Trp Val Lys Phe Leu Trp Asp His Thr Gly
        145                 150                 155 agt gtt ttg gac ctt ctt cga aac aat tct aga gta gag cgc ctt tac    649
Ser Val Leu Asp Leu Leu Arg Asn Asn Ser Arg Val Glu Arg Leu Tyr
    160                 165                 170
```

-continued

| | |
|---|---|
| cat gat atc gcc caa caa gct ttc aaa ttc tgc ctc cag tat act cgg<br>His Asp Ile Ala Gln Gln Ala Phe Lys Phe Cys Leu Gln Tyr Thr Arg<br>175                         180                      185                    190 | 697 |
| aag gct gag ttc cgc aag cta tgt gac aac ttg cga atc gac tta tcc<br>Lys Ala Glu Phe Arg Lys Leu Cys Asp Asn Leu Arg Ile Asp Leu Ser<br>                  195                      200                      205 | 745 |
| cag att cag cgc cac cat aac caa agc aca gca att aat ctt aat aat<br>Gln Ile Gln Arg His His Asn Gln Ser Thr Ala Ile Asn Leu Asn Asn<br>210                         215                      220 | 793 |
| cca gag agc cag tct atg cat ttg gaa acc aga ctt gtt cag ttg gac<br>Pro Glu Ser Gln Ser Met His Leu Glu Thr Arg Leu Val Gln Leu Asp<br>         225                      230                      235 | 841 |
| agt gct atc agc atg gaa tta tgg cag gaa gcc ttc aaa gct gtg gaa<br>Ser Ala Ile Ser Met Glu Leu Trp Gln Glu Ala Phe Lys Ala Val Glu<br>240                         245                      250 | 889 |
| gat att cat gga cta ttt tcc ttg tct aag aaa cca cct aag cct cag<br>Asp Ile His Gly Leu Phe Ser Leu Ser Lys Lys Pro Pro Lys Pro Gln<br>255                       260                      265                      270 | 937 |
| ttg atg gca aat tac tat aac aaa gtt tca aca gtg ttt tgg aaa tct<br>Leu Met Ala Asn Tyr Tyr Asn Lys Val Ser Thr Val Phe Trp Lys Ser<br>                  275                      280                      285 | 985 |
| gga aat gct ttg ttc cat gca tct aca ctt cat cgt ctt tat cat ctg<br>Gly Asn Ala Leu Phe His Ala Ser Thr Leu His Arg Leu Tyr His Leu<br>290                         295                      300 | 1033 |
| tct aga gaa atg aga aag aat ctt aca caa gaa gag atg caa aga atg<br>Ser Arg Glu Met Arg Lys Asn Leu Thr Gln Glu Glu Met Gln Arg Met<br>         305                      310                      315 | 1081 |
| tct act aga gtc ctt ttg gcg act ctt tcc att cct att act cct gag<br>Ser Thr Arg Val Leu Leu Ala Thr Leu Ser Ile Pro Ile Thr Pro Glu<br>320                         325                      330 | 1129 |
| cga act gat att gct cga ctt ttg gat atg gat ggt att ata gtt gag<br>Arg Thr Asp Ile Ala Arg Leu Leu Asp Met Asp Gly Ile Ile Val Glu<br>335                       340                      345                      350 | 1177 |
| aag cag cga cgc ctt gcc aca ttg cta ggt ctt caa gcc cca ccc aca<br>Lys Gln Arg Arg Leu Ala Thr Leu Leu Gly Leu Gln Ala Pro Pro Thr<br>                  355                      360                      365 | 1225 |
| cga atc ggc cta att aat gat atg gtc agg ttc agt gtg cta cag tat<br>Arg Ile Gly Leu Ile Asn Asp Met Val Arg Phe Ser Val Leu Gln Tyr<br>                  370                      375                      380 | 1273 |
| gtt gtc cca gaa gtg aaa gac ctt tac aac tgg ttg gag gtg gaa ttc<br>Val Val Pro Glu Val Lys Asp Leu Tyr Asn Trp Leu Glu Val Glu Phe<br>                     385                      390                      395 | 1321 |
| aac cca cta aaa ctc tgt gag aga gtt aca aag gta tta aat tgg gtt<br>Asn Pro Leu Lys Leu Cys Glu Arg Val Thr Lys Val Leu Asn Trp Val<br>400                         405                      410 | 1369 |
| agg gaa caa cct gaa aaa gaa cca gaa ttg caa caa tat gta cca caa<br>Arg Glu Gln Pro Glu Lys Glu Pro Glu Leu Gln Gln Tyr Val Pro Gln<br>415                         420                      425                      430 | 1417 |
| ctc cag aac aat acc ata ctc cgc ctt ctg caa cag gtg gca cag att<br>Leu Gln Asn Asn Thr Ile Leu Arg Leu Leu Gln Gln Val Ala Gln Ile<br>                  435                      440                      445 | 1465 |
| tat cag agc att gag ttt tct cgt ttg act tct ctg gtt cct ttt gtt<br>Tyr Gln Ser Ile Glu Phe Ser Arg Leu Thr Ser Leu Val Pro Phe Val<br>         450                      455                      460 | 1513 |
| gat gct ttc caa ctg gaa cgg gcc ata gta gat gca gcc agg cac tgt<br>Asp Ala Phe Gln Leu Glu Arg Ala Ile Val Asp Ala Ala Arg His Cys<br>465                         470                      475 | 1561 |
| gac ctg cag gta cgt att gac cat act tcc cgg act ctg agt ttt gga<br>Asp Leu Gln Val Arg Ile Asp His Thr Ser Arg Thr Leu Ser Phe Gly<br>         480                      485                      490 | 1609 |

-continued

| | | |
|---|---|---|
| tca gat ttg aat tat gca act cga gaa gat gcc cca gtt ggc cct cat<br>Ser Asp Leu Asn Tyr Ala Thr Arg Glu Asp Ala Pro Val Gly Pro His<br>495                    500                    505                    510 | 1657 |
| ctg cag agc atg cct tca gag cag ata aga aac cag ctc acg gcc atg<br>Leu Gln Ser Met Pro Ser Glu Gln Ile Arg Asn Gln Leu Thr Ala Met<br>                    515                    520                    525 | 1705 |
| tcc tca gtg ctt gcc aaa gca ctt gaa gtc atc aga cct gct cac att<br>Ser Ser Val Leu Ala Lys Ala Leu Glu Val Ile Arg Pro Ala His Ile<br>                530                    535                    540 | 1753 |
| ctg caa gag aaa gaa gaa cag cat caa ttg gca gtt aat gca tat ctt<br>Leu Gln Glu Lys Glu Glu Gln His Gln Leu Ala Val Asn Ala Tyr Leu<br>          545                    550                    555 | 1801 |
| aaa aat tca aga aaa gag cac cag agg atc ctg gct cgg aga cag aca<br>Lys Asn Ser Arg Lys Glu His Gln Arg Ile Leu Ala Arg Arg Gln Thr<br>560                    565                    570 | 1849 |
| att gag gaa aga aaa gag cgt ctt gag agt ctg aat att caa cgt gag<br>Ile Glu Glu Arg Lys Glu Arg Leu Glu Ser Leu Asn Ile Gln Arg Glu<br>575                    580                    585                    590 | 1897 |
| aag gaa gaa ctc gag cag agg gaa gct gaa ctc cag aag tac gaa agg<br>Lys Glu Glu Leu Glu Gln Arg Glu Ala Glu Leu Gln Lys Tyr Glu Arg<br>                    595                    600                    605 | 1945 |
| ctg aag aag aaa ggc tgc caa gag gca aag gag cga gag aag gaa cga<br>Leu Lys Lys Lys Gly Cys Gln Glu Ala Lys Glu Arg Glu Lys Glu Arg<br>                610                    615                    620 | 1993 |
| atc ctt caa gaa cac gag caa atc aag aag aaa act gtt cgg gag cgg<br>Ile Leu Gln Glu His Glu Gln Ile Lys Lys Lys Thr Val Arg Glu Arg<br>          625                    630                    635 | 2041 |
| tta gag cag atc aag aag aca gag ctg ggc gcc aaa gca ttt aaa gat<br>Leu Glu Gln Ile Lys Lys Thr Glu Leu Gly Ala Lys Ala Phe Lys Asp<br>640                    645                    650 | 2089 |
| att gac att gaa gac ctt gaa gaa ctg gat cca gat ttt att atg gcc<br>Ile Asp Ile Glu Asp Leu Glu Glu Leu Asp Pro Asp Phe Ile Met Ala<br>655                    660                    665                    670 | 2137 |
| aaa cag gtt gaa caa ctg gag aaa gaa aag aag gaa ctt cag gaa cgc<br>Lys Gln Val Glu Gln Leu Glu Lys Glu Lys Lys Glu Leu Gln Glu Arg<br>                    675                    680                    685 | 2185 |
| ctg aag aat caa gaa aag aag att gac tat ttt gag aga gct aag cgt<br>Leu Lys Asn Gln Glu Lys Lys Ile Asp Tyr Phe Glu Arg Ala Lys Arg<br>                690                    695                    700 | 2233 |
| ttg gaa gaa att cct tta ata aag agt gct tat gag gaa caa agg gtt<br>Leu Glu Glu Ile Pro Leu Ile Lys Ser Ala Tyr Glu Glu Gln Arg Val<br>          705                    710                    715 | 2281 |
| aaa gac atg gac ctg tgg gaa cag caa gaa gaa gaa aga atc act aca<br>Lys Asp Met Asp Leu Trp Glu Gln Gln Glu Glu Glu Arg Ile Thr Thr<br>720                    725                    730 | 2329 |
| atg cag cta gaa cga gaa aaa gct ctg gag cat aag aat agg atg tca<br>Met Gln Leu Glu Arg Glu Lys Ala Leu Glu His Lys Asn Arg Met Ser<br>735                    740                    745                    750 | 2377 |
| cga atg ttg gaa gac aga gat cta ttt gtg atg cgc ctc aaa gct gcc<br>Arg Met Leu Glu Asp Arg Asp Leu Phe Val Met Arg Leu Lys Ala Ala<br>                    755                    760                    765 | 2425 |
| cgg cag tct gtc tac gag gaa aaa ctg aaa cag ttt gaa gag cgc tta<br>Arg Gln Ser Val Tyr Glu Glu Lys Leu Lys Gln Phe Glu Glu Arg Leu<br>          770                    775                    780 | 2473 |
| gca gaa gaa agg cat agt cgc cta gaa gat cgg aaa agg cag cgg aaa<br>Ala Glu Glu Arg His Ser Arg Leu Glu Asp Arg Lys Arg Gln Arg Lys<br>                785                    790                    795 | 2521 |
| gaa gaa cgc aaa ata act tat tac aga gaa agg aag aag aag agc aga<br>Glu Glu Arg Lys Ile Thr Tyr Tyr Arg Glu Arg Lys Lys Lys Ser Arg | 2569 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 800 |     |     |     |     | 805 |     |     |     |     | 810 |     |     |      |
| gga | ggg | cag | agg | agc | aga | tgc | tca | aag | acg | gag | aag | aaa | gag | aac | gtg | 2617 |
| Gly | Gly | Gln | Arg | Ser | Arg | Cys | Ser | Lys | Thr | Glu | Lys | Lys | Glu | Asn | Val |      |
| 815 |     |     |     |     | 820 |     |     |     |     | 825 |     |     |     |     | 830 |      |
| ctg | aga | gag | caa | aac | gcg | gag | gaa | gaa | ctt | aga | gag | tat | cag | gag | cga | 2665 |
| Leu | Arg | Glu | Gln | Asn | Ala | Glu | Glu | Glu | Leu | Arg | Glu | Tyr | Gln | Glu | Arg |      |
|     |     |     |     | 835 |     |     |     |     | 840 |     |     |     |     | 845 |     |      |
| gtc | aag | aaa | cta | gaa | gaa | gta | gaa | agg | aaa | aag | cgg | caa | aga | gag | ctg | 2713 |
| Val | Lys | Lys | Leu | Glu | Glu | Val | Glu | Arg | Lys | Lys | Arg | Gln | Arg | Glu | Leu |      |
|     |     |     | 850 |     |     |     |     | 855 |     |     |     |     | 860 |     |     |      |
| gaa | att | gaa | gaa | agg | gaa | agg | cgc | aga | gag | gaa | gaa | agg | aga | ctt | ggt | 2761 |
| Glu | Ile | Glu | Glu | Arg | Glu | Arg | Arg | Arg | Glu | Glu | Glu | Arg | Arg | Leu | Gly |      |
|     |     | 865 |     |     |     |     | 870 |     |     |     |     | 875 |     |     |     |      |
| gat | gat | cca | ctt | tct | agg | aag | gac | tct | cgg | tgg | gga | gat | aga | gat | tca | 2809 |
| Asp | Asp | Pro | Leu | Ser | Arg | Lys | Asp | Ser | Arg | Trp | Gly | Asp | Arg | Asp | Ser |      |
|     | 880 |     |     |     |     | 885 |     |     |     |     | 890 |     |     |     |     |      |
| gaa | ggc | acc | tgg | agg | aaa | gga | cca | gaa | gct | gac | tct | gag | tgg | aga | aga | 2857 |
| Glu | Gly | Thr | Trp | Arg | Lys | Gly | Pro | Glu | Ala | Asp | Ser | Glu | Trp | Arg | Arg |      |
| 895 |     |     |     |     | 900 |     |     |     |     | 905 |     |     |     |     | 910 |      |
| ggc | cca | cca | gaa | aag | gag | tgg | aga | cga | gaa | act | cgg | gat | gat | gag | agg | 2905 |
| Gly | Pro | Pro | Glu | Lys | Glu | Trp | Arg | Arg | Glu | Thr | Arg | Asp | Asp | Glu | Arg |      |
|     |     |     |     | 915 |     |     |     |     | 920 |     |     |     |     | 925 |     |      |
| cct | cac | agg | aga | gat | gag | gat | cgg | ctg | agg | cgc | ttg | ggg | ggt | gac | gat | 2953 |
| Pro | His | Arg | Arg | Asp | Glu | Asp | Arg | Leu | Arg | Arg | Leu | Gly | Gly | Asp | Asp |      |
|     |     |     | 930 |     |     |     |     | 935 |     |     |     |     | 940 |     |     |      |
| gaa | gag | aga | gag | tct | tct | ctt | aga | ccg | gat | gat | gat | cgt | atc | ccc | agg | 3001 |
| Glu | Glu | Arg | Glu | Ser | Ser | Leu | Arg | Pro | Asp | Asp | Asp | Arg | Ile | Pro | Arg |      |
|     |     | 945 |     |     |     |     | 950 |     |     |     |     | 955 |     |     |     |      |
| cgt | ggc | ctg | gat | gat | gac | aga | ggg | cct | aga | cgt | ggt | ccc | gat | gaa | gat | 3049 |
| Arg | Gly | Leu | Asp | Asp | Asp | Arg | Gly | Pro | Arg | Arg | Gly | Pro | Asp | Glu | Asp |      |
|     | 960 |     |     |     |     | 965 |     |     |     |     | 970 |     |     |     |     |      |
| aga | ttt | tct | cgt | aga | gga | aca | gat | gat | gac | cgt | cct | tcc | tgg | cgt | aat | 3097 |
| Arg | Phe | Ser | Arg | Arg | Gly | Thr | Asp | Asp | Asp | Arg | Pro | Ser | Trp | Arg | Asn |      |
| 975 |     |     |     |     | 980 |     |     |     |     | 985 |     |     |     |     | 990 |      |
| gca | gat | gat | gat | agg | cct | ccc | agg | cga | att | ggt | gat | gat | gac | agg | gga | 3145 |
| Ala | Asp | Asp | Asp | Arg | Pro | Pro | Arg | Arg | Ile | Gly | Asp | Asp | Asp | Arg | Gly |      |
|     |     |     |     | 995 |     |     |     |     | 1000|     |     |     |     | 1005|     |      |
| agc | tgg | cgt | cac | aca | gat | gac | gac | aga | cca | ccc | aga | cgg | gga | ctg | gat | 3193 |
| Ser | Trp | Arg | His | Thr | Asp | Asp | Asp | Arg | Pro | Pro | Arg | Arg | Gly | Leu | Asp |      |
|     |     |     | 1010|     |     |     |     | 1015|     |     |     |     | 1020|     |     |      |
| gat | gag | aga | gga | agc | tgg | cgt | aca | gca | gat | gag | gac | aga | gga | cct | aga | 3241 |
| Asp | Glu | Arg | Gly | Ser | Trp | Arg | Thr | Ala | Asp | Glu | Asp | Arg | Gly | Pro | Arg |      |
|     |     | 1025|     |     |     |     | 1030|     |     |     |     | 1035|     |     |     |      |
| cga | ggg | atg | gat | gat | gac | cgg | ggg | cca | aga | cga | gga | ggt | gct | gat | gat | 3289 |
| Arg | Gly | Met | Asp | Asp | Asp | Arg | Gly | Pro | Arg | Arg | Gly | Gly | Ala | Asp | Asp |      |
|     | 1040|     |     |     |     | 1045|     |     |     |     | 1050|     |     |     |     |      |
| gaa | cgg | tca | tct | ggc | gga | atg | ctg | atg | atg | ata | ggg | gtc | cca | gga | gag | 3337 |
| Glu | Arg | Ser | Ser | Gly | Gly | Met | Leu | Met | Met | Ile | Gly | Val | Pro | Gly | Glu |      |
| 1055|     |     |     | 1060|     |     |     |     | 1065|     |     |     |     | 1070|     |      |
| gca | tgg | atg | atg | ata | ggg | gtc | cca | ggc | gag | ggc | tgg | atg | atg | acc | gag | 3385 |
| Ala | Trp | Met | Met | Ile | Gly | Val | Pro | Gly | Glu | Gly | Trp | Met | Met | Thr | Glu |      |
|     |     |     | 1075|     |     |     |     | 1080|     |     |     |     | 1085|     |     |      |
| gac | ctt | gga | gga | atg | ctg | ctg | aag | ata | gga | ttt | cca | gga | gag | gtg | cag | 3433 |
| Asp | Leu | Gly | Gly | Met | Leu | Leu | Lys | Ile | Gly | Phe | Pro | Gly | Glu | Val | Gln |      |
|     |     | 1090|     |     |     |     | 1095|     |     |     |     | 1100|     |     |     |      |
| atg | atg | acc | gag | ggc | ctt | gga | gaa | ata | tgg | atg | atg | ata | ggg | ttc | cta | 3481 |
| Met | Met | Thr | Glu | Gly | Leu | Gly | Glu | Ile | Trp | Met | Met | Ile | Gly | Phe | Leu |      |
|     | 1105|     |     |     |     | 1110|     |     |     |     | 1115|     |     |     |     |      |
| gaa | ggg | gtg | atg | atg | caa | gac | ctg | gtc | ctt | gga | gac | cat | ttg | tca | agc | 3529 |

```
         Glu Gly Val Met Met Gln Asp Leu Val Leu Gly Asp His Leu Ser Ser
            1120                1125                1130 cag gtg gat gga gag aga aag aaa agg cta gag aag aga gtt ggg gtc      3577
Gln Val Asp Gly Glu Arg Lys Lys Arg Leu Glu Lys Arg Val Gly Val
1135                1140                1145                1150 cac ctc gag aat caa gac cat cag aag aac gtg aat ggg ata gag aca      3625
His Leu Glu Asn Gln Asp His Gln Lys Asn Val Asn Gly Ile Glu Thr
                1155                1160                1165 aag aga agg aca gag ata atc aag atc gag agg aga atg aca aag acc      3673
Lys Arg Arg Thr Glu Ile Ile Lys Ile Glu Arg Arg Met Thr Lys Thr
            1170                1175                1180 ttg aac gag ata ggg aca gag aga gag atg ggg acc ggg agg att cga      3721
Leu Asn Glu Ile Gly Thr Glu Arg Glu Met Gly Thr Gly Arg Ile Arg
        1185                1190                1195 ttc aga aga ccc agg gat gaa ggt ggc tgg aga aga gga cca gca gaa      3769
Phe Arg Arg Pro Arg Asp Glu Gly Gly Trp Arg Arg Gly Pro Ala Glu
    1200                1205                1210 gaa tct tca agc tgg aga gat tca agt cgc cgt gat gat agg gac agg      3817
Glu Ser Ser Ser Trp Arg Asp Ser Ser Arg Arg Asp Asp Arg Asp Arg
1215                1220                1225                1230 gaa gac cgt cga cgg gat aga gat gat cgt cgt gat ctg aga gac ctg      3865
Glu Asp Arg Arg Arg Asp Arg Asp Asp Arg Arg Asp Leu Arg Asp Leu
                1235                1240                1245 aga gac aga agg gat tta aga gat gat aga gat cgg aga gga cct ccc      3913
Arg Asp Arg Arg Asp Leu Arg Asp Asp Arg Asp Arg Arg Gly Pro Pro
            1250                1255                1260 ctc aga tca gag cga gaa gaa gca agc tct tgg aga cgc act gat gac      3961
Leu Arg Ser Glu Arg Glu Glu Ala Ser Ser Trp Arg Arg Thr Asp Asp
        1265                1270                1275 agg aaa gat gac cgg act gaa gag agg gat cca cct cgt cgt gtt cct      4009
Arg Lys Asp Asp Arg Thr Glu Glu Arg Asp Pro Pro Arg Arg Val Pro
    1280                1285                1290 ccc cca gct ctt tca aga gat cga gaa aga gag cga gaa cga gaa ggt      4057
Pro Pro Ala Leu Ser Arg Asp Arg Glu Arg Glu Arg Glu Arg Glu Gly
1295                1300                1305                1310 gag aaa gag aaa gca tcc tgg aga gct gag aaa gat agg gag tcc ctt      4105
Glu Lys Glu Lys Ala Ser Trp Arg Ala Glu Lys Asp Arg Glu Ser Leu
                1315                1320                1325 cgt cgt act aag aat gaa act gat gaa gat gga tgg acc aca gta cga      4153
Arg Arg Thr Lys Asn Glu Thr Asp Glu Asp Gly Trp Thr Thr Val Arg
            1330                1335                1340 cgt t aagtcccaag atgatggagt caaacttgtg gcttacatag gtttgatcac         4207
Arg attcaaggat tattatactt gtgcttcaac cagtctaaat tgaattcttt aatgttgtct    4267
caccataaca caaaaagcat gaacttgtat taatcatata taatagattg atcatgcact    4327
gtattcacag gaggttggaa aaccatgcca ttttctggaa cttaaggtgt tgcattattt    4387
catcaatcat ttgttaaaaa aaaaaaacta aaaaataaaa atgtgaaccc ttcagtgtaa    4447 acacctatc ttggtataca atgatctttt tgttttgttt tgaagtatca gatattaatt     4507
tggaataagg taaggttctc ttgaaacatt tgaaacccct ttaagccaac tgatctgaca    4567
gctttcccat cagtagaagt gggaacatac cttcttaggt atttactatt aactacatgt    4627
aggcagttta tagcttctga tcagttagta gacattacaa acactggttg taatgggtt     4687 ttctgtagac tttacttgag aggtgagtat aaagcatttt ttagtcatca tcatgacgat    4747
gctgctcaag tgcagatcca gaacagtaca gcgttgggtt cctagagcat ttggtaaact    4807
gttgtgggtt ttttctttct gttgccaaaa ctgcttttcc actaattcat gcctttcaag    4867
```

```
cattttaaat atgacaatat ttataaatgt gtggtttgga ggaattgttt aaattctttt    4927
tcctaatttt cttttttcag gatagattat ttcaacaagt aatttgtagt gatgactgtg    4987
ttgacttcaa ttttggagtg tagtagctgt gtttaaaaaa aagagtaata accatttggt    5047
cttattgaag ccaacacgga atttgctgct gtgttttttt ctttggtgat aaataaaata    5107
cttacataat tggaaaaaaa aaaaaaaaaa                                     5137
```

<210> SEQ ID NO 2
<211> LENGTH: 1343
<212> TYPE: PRT
<213> ORGANISM: Mus sp.

<400> SEQUENCE: 2

```
Met Pro Ala Tyr Phe Gln Arg Pro Glu Asn Ala Leu Lys Arg Ala Asn
  1               5                  10                  15

Glu Phe Leu Glu Val Gly Lys Lys Gln Pro Ala Leu Asp Val Leu Tyr
             20                  25                  30

Asp Val Met Lys Ser Lys Lys His Arg Thr Trp Gln Lys Ile His Glu
         35                  40                  45

Pro Ile Met Leu Lys Tyr Leu Glu Leu Cys Val Asp Leu Arg Lys Ser
     50                  55                  60

His Leu Ala Lys Glu Gly Leu Tyr Gln Tyr Lys Asn Ile Cys Gln Gln
 65                  70                  75                  80

Val Asn Ile Lys Ser Leu Glu Asp Val Val Arg Ala Tyr Leu Lys Leu
                 85                  90                  95

Ala Glu Glu Lys Thr Glu Ala Ala Lys Glu Glu Ser Gln Gln Met Val
            100                 105                 110

Leu Asp Ile Glu Asp Leu Asp Asn Ile Gln Thr Pro Glu Ser Val Leu
        115                 120                 125

Leu Ser Ala Val Ser Gly Glu Asp Thr Gln Asp Arg Thr Asp Arg Leu
    130                 135                 140

Leu Leu Thr Pro Trp Val Lys Phe Leu Trp Asp His Thr Gly Ser Val
145                 150                 155                 160

Leu Asp Leu Leu Arg Asn Asn Ser Arg Val Glu Arg Leu Tyr His Asp
                165                 170                 175

Ile Ala Gln Gln Ala Phe Lys Phe Cys Leu Gln Tyr Thr Arg Lys Ala
            180                 185                 190

Glu Phe Arg Lys Leu Cys Asp Asn Leu Arg Ile Asp Leu Ser Gln Ile
        195                 200                 205

Gln Arg His His Asn Gln Ser Thr Ala Ile Asn Leu Asn Asn Pro Glu
    210                 215                 220

Ser Gln Ser Met His Leu Glu Thr Arg Leu Val Gln Leu Asp Ser Ala
225                 230                 235                 240

Ile Ser Met Glu Leu Trp Gln Glu Ala Phe Lys Ala Val Glu Asp Ile
                245                 250                 255

His Gly Leu Phe Ser Leu Ser Lys Lys Pro Lys Pro Gln Leu Met
            260                 265                 270

Ala Asn Tyr Tyr Asn Lys Val Ser Thr Val Phe Trp Lys Ser Gly Asn
        275                 280                 285

Ala Leu Phe His Ala Ser Thr Leu His Arg Leu Tyr His Leu Ser Arg
    290                 295                 300

Glu Met Arg Lys Asn Leu Thr Gln Glu Glu Met Gln Arg Met Ser Thr
305                 310                 315                 320
```

-continued

```
Arg Val Leu Leu Ala Thr Leu Ser Ile Pro Ile Thr Pro Glu Arg Thr
            325                 330                 335

Asp Ile Ala Arg Leu Leu Asp Met Asp Gly Ile Ile Val Glu Lys Gln
            340                 345                 350

Arg Arg Leu Ala Thr Leu Leu Gly Leu Gln Ala Pro Pro Thr Arg Ile
            355                 360                 365

Gly Leu Ile Asn Asp Met Val Arg Phe Ser Val Leu Gln Tyr Val Val
    370                 375                 380

Pro Glu Val Lys Asp Leu Tyr Asn Trp Leu Glu Val Glu Phe Asn Pro
385                 390                 395                 400

Leu Lys Leu Cys Glu Arg Val Thr Lys Val Leu Asn Trp Val Arg Glu
            405                 410                 415

Gln Pro Glu Lys Glu Pro Glu Leu Gln Gln Tyr Val Pro Gln Leu Gln
            420                 425                 430

Asn Asn Thr Ile Leu Arg Leu Leu Gln Gln Val Ala Gln Ile Tyr Gln
            435                 440                 445

Ser Ile Glu Phe Ser Arg Leu Thr Ser Leu Val Pro Phe Val Asp Ala
    450                 455                 460

Phe Gln Leu Glu Arg Ala Ile Val Asp Ala Ala Arg His Cys Asp Leu
465                 470                 475                 480

Gln Val Arg Ile Asp His Thr Ser Arg Thr Leu Ser Phe Gly Ser Asp
            485                 490                 495

Leu Asn Tyr Ala Thr Arg Glu Asp Ala Pro Val Gly Pro His Leu Gln
            500                 505                 510

Ser Met Pro Ser Glu Gln Ile Arg Asn Gln Leu Thr Ala Met Ser Ser
            515                 520                 525

Val Leu Ala Lys Ala Leu Glu Val Ile Arg Pro Ala His Ile Leu Gln
    530                 535                 540

Glu Lys Glu Glu Gln His Gln Leu Ala Val Asn Ala Tyr Leu Lys Asn
545                 550                 555                 560

Ser Arg Lys Glu His Gln Arg Ile Leu Ala Arg Arg Gln Thr Ile Glu
            565                 570                 575

Glu Arg Lys Glu Arg Leu Glu Ser Leu Asn Ile Gln Arg Glu Lys Glu
            580                 585                 590

Glu Leu Glu Gln Arg Glu Ala Glu Leu Gln Lys Tyr Glu Arg Leu Lys
            595                 600                 605

Lys Lys Gly Cys Gln Glu Ala Lys Glu Arg Glu Lys Glu Arg Ile Leu
    610                 615                 620

Gln Glu His Glu Gln Ile Lys Lys Thr Val Arg Glu Arg Leu Glu
625                 630                 635                 640

Gln Ile Lys Lys Thr Glu Leu Gly Ala Lys Ala Phe Lys Asp Ile Asp
            645                 650                 655

Ile Glu Asp Leu Glu Glu Leu Asp Pro Asp Phe Ile Met Ala Lys Gln
            660                 665                 670

Val Glu Gln Leu Glu Lys Glu Lys Glu Leu Gln Glu Arg Leu Lys
            675                 680                 685

Asn Gln Glu Lys Lys Ile Asp Tyr Phe Glu Arg Ala Lys Arg Leu Glu
    690                 695                 700

Glu Ile Pro Leu Ile Lys Ser Ala Tyr Glu Gly Gln Arg Val Lys Asp
705                 710                 715                 720

Met Asp Leu Trp Glu Gln Gln Glu Glu Arg Ile Thr Thr Met Gln
            725                 730                 735

Leu Glu Arg Glu Lys Ala Leu Glu His Lys Asn Arg Met Ser Arg Met
```

-continued

```
                740               745               750
Leu Glu Asp Arg Asp Leu Phe Val Met Arg Leu Lys Ala Ala Arg Gln
            755               760               765
Ser Val Tyr Glu Glu Lys Leu Lys Gln Phe Glu Arg Leu Ala Glu
    770               775               780
Glu Arg His Ser Arg Leu Glu Asp Arg Lys Arg Gln Arg Lys Glu Glu
785               790               795               800
Arg Lys Ile Thr Tyr Tyr Arg Glu Arg Lys Lys Ser Arg Gly Gly
                805               810               815
Gln Arg Ser Arg Cys Ser Lys Thr Glu Lys Lys Glu Asn Val Leu Arg
            820               825               830
Glu Gln Asn Ala Glu Glu Glu Leu Arg Glu Tyr Gln Glu Arg Val Lys
        835               840               845
Lys Leu Glu Glu Val Glu Arg Lys Lys Arg Gln Arg Glu Leu Glu Ile
    850               855               860
Glu Glu Arg Glu Arg Arg Arg Glu Glu Arg Arg Leu Gly Asp Asp
865               870               875               880
Pro Leu Ser Arg Lys Asp Ser Arg Trp Gly Asp Arg Asp Ser Glu Gly
                885               890               895
Thr Trp Arg Lys Gly Pro Glu Ala Asp Ser Glu Trp Arg Arg Gly Pro
            900               905               910
Pro Glu Lys Glu Trp Arg Arg Glu Thr Arg Asp Asp Glu Arg Pro His
        915               920               925
Arg Arg Asp Glu Asp Arg Leu Arg Leu Gly Gly Asp Asp Glu Glu
930               935               940
Arg Glu Ser Ser Leu Arg Pro Asp Asp Arg Ile Pro Arg Arg Gly
945               950               955               960
Leu Asp Asp Asp Arg Gly Pro Arg Arg Gly Pro Asp Glu Asp Arg Phe
                965               970               975
Ser Arg Arg Gly Thr Asp Asp Asp Arg Pro Ser Trp Arg Asn Ala Asp
            980               985               990
Asp Asp Arg Pro Pro Arg Arg Ile Gly Asp Asp Asp Arg Gly Ser Trp
        995              1000              1005
Arg His Thr Asp Asp Asp Arg Pro Pro Arg Arg Gly Leu Asp Asp Glu
    1010              1015              1020
Arg Gly Ser Trp Arg Thr Ala Asp Glu Asp Arg Gly Pro Arg Arg Gly
1025              1030              1035              1040
Met Asp Asp Asp Arg Gly Pro Arg Arg Gly Gly Ala Asp Asp Glu Arg
                1045              1050              1055
Ser Ser Gly Gly Met Leu Met Met Ile Gly Val Pro Gly Glu Ala Trp
            1060              1065              1070
Met Met Ile Gly Val Pro Gly Glu Gly Trp Met Met Thr Glu Asp Leu
        1075              1080              1085
Gly Gly Met Leu Leu Lys Ile Gly Phe Pro Gly Glu Val Gln Met Met
    1090              1095              1100
Thr Glu Gly Leu Gly Glu Ile Trp Met Met Ile Gly Phe Leu Glu Gly
1105              1110              1115              1120
Val Met Met Gln Asp Leu Val Leu Gly Asp His Leu Ser Ser Gln Val
                1125              1130              1135
Asp Gly Glu Arg Lys Lys Arg Leu Glu Lys Arg Val Gly Val His Leu
            1140              1145              1150
Glu Asn Gln Asp His Gln Lys Asn Val Asn Gly Ile Glu Thr Lys Arg
        1155              1160              1165
```

-continued

Arg Thr Glu Ile Ile Lys Ile Glu Arg Arg Met Thr Lys Thr Leu Asn
　　 1170　　　　　　　　1175　　　　　　　　1180

Glu Ile Gly Thr Glu Arg Glu Met Gly Thr Gly Arg Ile Arg Phe Arg
1185　　　　　　　　1190　　　　　　　　1195　　　　　　　　1200

Arg Pro Arg Asp Glu Gly Gly Trp Arg Gly Pro Ala Glu Glu Ser
　　　　　　1205　　　　　　　　1210　　　　　　　　1215

Ser Ser Trp Arg Asp Ser Ser Arg Arg Asp Asp Arg Asp Arg Glu Asp
　　　 1220　　　　　　　　1225　　　　　　　　1230

Arg Arg Arg Asp Arg Asp Asp Arg Arg Asp Leu Arg Asp Leu Arg Asp
　　　 1235　　　　　　　　1240　　　　　　　　1245

Arg Arg Asp Leu Arg Asp Asp Arg Asp Arg Arg Gly Pro Pro Leu Arg
　　　 1250　　　　　　　　1255　　　　　　　　1260

Ser Glu Arg Glu Glu Ala Ser Ser Trp Arg Arg Thr Asp Asp Arg Lys
1265　　　　　　　　1270　　　　　　　　1275　　　　　　　　1280

Asp Asp Arg Thr Glu Glu Arg Asp Pro Pro Arg Arg Val Pro Pro Pro
　　　　　　1285　　　　　　　　1290　　　　　　　　1295

Ala Leu Ser Arg Asp Arg Glu Arg Glu Arg Glu Arg Glu Gly Glu Lys
　　　　　 1300　　　　　　　　1305　　　　　　　　1310

Glu Lys Ala Ser Trp Arg Ala Glu Lys Asp Arg Glu Ser Leu Arg Arg
　　　　　 1315　　　　　　　　1320　　　　　　　　1325

Thr Lys Asn Glu Thr Asp Glu Asp Gly Trp Thr Thr Val Arg Arg
　　　　　 1330　　　　　　　　1335　　　　　　　　1340

<210> SEQ ID NO 3
<211> LENGTH: 276
<212> TYPE: PRT
<213> ORGANISM: Mus sp.
<220> FEATURE:
<223> OTHER INFORMATION: peptide

<400> SEQUENCE: 3

Met Pro Ser Glu Gln Ile Arg Asn Gln Leu Thr Ala Met Ser Ser Val
　1　　　　　　　　5　　　　　　　　10　　　　　　　　15

Leu Ala Lys Ala Ile Glu Val Ile Arg Pro Ala His Ile Leu Gln Glu
　　　　　　　 20　　　　　　　　25　　　　　　　　30

Lys Glu Glu Gln His Gln Leu Ala Val Asn Ala Tyr Leu Lys Asn Ser
　　　　　 35　　　　　　　　40　　　　　　　　45

Arg Lys Glu His Gln Arg Ile Leu Ala Arg Arg Gln Thr Ile Glu Glu
　　　 50　　　　　　　　55　　　　　　　　60

Arg Lys Glu Arg Leu Glu Ser Leu Asn Ile Gln Arg Glu Lys Glu Glu
65　　　　　　　　70　　　　　　　　75　　　　　　　　80

Leu Glu Gln Arg Glu Ala Glu Leu Gln Lys Val Arg Lys Ala Glu Glu
　　　　　　　　85　　　　　　　　90　　　　　　　　95

Glu Arg Leu Pro Arg Gly Lys Gly Ala Arg Glu Gly Thr Asn Pro Ser
　　　　　　　 100　　　　　　　 105　　　　　　　　110

Arg Thr Arg Ala Asn Gln Glu Glu Asn Cys Ser Gly Ala Val Arg Ala
　　　　　 115　　　　　　　　120　　　　　　　　125

Asp Gln Glu Asp Arg Leu Gly Ala Lys Ala Phe Lys Asp Ile Asp Ile
　　　 130　　　　　　　　135　　　　　　　　140

Glu Asp Leu Glu Glu Leu Asp Pro Asp Phe Ile Met Ala Lys Gln Val
145　　　　　　　　150　　　　　　　　155　　　　　　　　160

Glu Gln Leu Glu Lys Glu Lys Lys Asp Tyr Gln Glu Arg Leu Lys Asn
　　　　　　　 165　　　　　　　　170　　　　　　　　175

Gln Glu Lys Lys Ile Asp Tyr Phe Glu Arg Ala Lys Arg Leu Glu Glu
　　　　　 180　　　　　　　　185　　　　　　　　190

```
Ile Pro Leu Ile Lys Ser Ala Tyr Glu His Arg Val Lys Asp Met
            195                 200                 205

Asp Leu Trp Glu Gln Gln Glu Glu Arg Ile Thr Thr Met Gln Leu
        210                 215                 220

Glu Arg Glu Lys Ala Leu Glu His Lys Asn Arg Met Ser Arg Met Leu
225                 230                 235                 240

Glu Asp Arg Asp Leu Phe Val Met Arg Leu Lys Val Ala Arg Gln Ser
                245                 250                 255

Val Tyr Glu Glu Lys Leu Lys Gln Phe Glu Glu Arg Leu Ala Glu Glu
                260                 265                 270

Ser Ile Val Ala
        275

<210> SEQ ID NO 4
<211> LENGTH: 447
<212> TYPE: PRT
<213> ORGANISM: Mus sp.
<220> FEATURE:
<223> OTHER INFORMATION: peptide

<400> SEQUENCE: 4

Met Pro Ser Glu Gln Ile Arg Asn Gln Leu Thr Ala Met Ser Ser Val
  1               5                  10                  15

Leu Ala Lys Ala Ile Glu Val Ile Arg Pro Ala His Ile Leu Gln Glu
                 20                  25                  30

Lys Glu Glu Gln His Gln Leu Ala Val Asn Ala Tyr Leu Lys Asn Ser
             35                  40                  45

Arg Lys Glu His Gln Arg Ile Leu Ala Arg Arg Gln Thr Ile Glu Glu
    50                  55                  60

Arg Lys Glu Arg Leu Glu Ser Leu Asn Ile Gln Arg Glu Lys Glu Glu
65                  70                  75                  80

Leu Glu Gln Arg Glu Ala Glu Leu Gln Lys Val Arg Lys Ala Glu Glu
                85                  90                  95

Glu Arg Leu Pro Arg Gly Lys Gly Ala Arg Glu Gly Thr Asn Pro Ser
            100                 105                 110

Arg Thr Arg Ala Asn Gln Glu Glu Asn Cys Ser Gly Ala Val Arg Ala
        115                 120                 125

Asp Gln Glu Asp Arg Leu Gly Ala Lys Ala Phe Lys Asp Ile Asp Ile
    130                 135                 140

Glu Asp Leu Glu Glu Leu Asp Pro Asp Phe Ile Met Ala Lys Gln Val
145                 150                 155                 160

Glu Gln Leu Glu Lys Glu Lys Lys Asp Tyr Gln Glu Arg Leu Lys Asn
                165                 170                 175

Gln Glu Lys Lys Ile Asp Tyr Phe Glu Arg Ala Lys Arg Leu Glu Glu
            180                 185                 190

Ile Pro Leu Ile Lys Ser Ala Tyr Glu Glu His Arg Val Lys Asp Met
        195                 200                 205

Asp Leu Trp Glu Gln Gln Glu Glu Arg Ile Thr Thr Met Gln Leu
    210                 215                 220

Glu Arg Glu Lys Ala Leu Glu His Lys Asn Arg Met Ser Arg Met Leu
225                 230                 235                 240

Glu Asp Arg Asp Leu Phe Val Met Arg Leu Lys Val Ala Arg Gln Ser
                245                 250                 255

Val Tyr Glu Glu Lys Leu Lys Gln Phe Glu Glu Arg Leu Ala Glu Glu
            260                 265                 270
```

-continued

```
Arg His Ser Arg Leu Glu Asp Arg Lys Arg Gln Arg Lys Glu Glu Arg
            275                 280                 285

Lys Ile Thr Tyr Tyr Arg Glu Lys Glu Glu Glu Gln Arg Arg Ala
290                 295                 300

Glu Glu Gln Met Leu Lys Glu Arg Glu Arg Glu Arg Ala Glu Arg
305                 310                 315                 320

Ala Lys Arg Glu Glu Glu Leu Arg Glu Tyr Gln Glu Arg Val Lys Lys
                325                 330                 335

Leu Glu Glu Val Glu Arg Lys Arg Gln Arg Glu Leu Glu Ile Glu
            340                 345                 350

Glu Arg Glu Arg Arg Glu Glu Arg Arg Leu Gly Asp Asp Pro
        355                 360                 365

Leu Ser Arg Lys Asp Ser Arg Trp Gly Asp Arg Asp Ser Glu Gly Thr
370                 375                 380

Trp Arg Lys Gly Pro Glu Ala Asp Ser Glu Trp Arg Arg Gly Pro Pro
385                 390                 395                 400

Glu Lys Glu Trp Arg Arg Glu Thr Arg Asp Asp Glu Arg Pro His Arg
                405                 410                 415

Arg Asp Glu Asp Arg Leu Arg Arg Leu Gly Gly Asp Glu Glu Arg
            420                 425                 430

Glu Ser Ser Leu Arg Pro Asp Asp Asp Arg Ile Pro Arg Arg Gly
        435                 440                 445
```

<210> SEQ ID NO 5
<211> LENGTH: 964
<212> TYPE: PRT
<213> ORGANISM: Saccharomyces sp.
<220> FEATURE:
<223> OTHER INFORMATION: peptide

<400> SEQUENCE: 5

```
Met Ala Pro Pro Phe Arg Pro Glu Asn Ala Ile Lys Arg Ala Asp
 1               5                  10                  15

Glu Leu Ile Ser Val Gly Glu Lys Gln Ala Ala Leu Gln Ser Leu His
            20                  25                  30

Asp Phe Ile Thr Ala Arg Arg Ile Arg Trp Ala Thr Pro Ser Thr Val
        35                  40                  45

Glu Pro Val Val Phe Lys Phe Leu Glu Ile Gly Val Glu Leu Lys Lys
    50                  55                  60

Gly Lys Leu Leu Lys Asp Gly Leu His Gln Tyr Lys Lys Leu Ile Gln
65                  70                  75                  80

Gly Ser Thr Glu Gly Leu Val Ser Val Gly Ala Val Ala Arg Lys Phe
                85                  90                  95

Ile Asp Leu Val Glu Ser Lys Ile Ala Ser Glu Gln Thr Arg Ala Asp
            100                 105                 110

Glu Leu Gln Lys Gln Glu Ile Asp Asp Leu Glu Gly Gly Val Thr
        115                 120                 125

Pro Glu Asn Leu Leu Ile Ser Val Tyr Glu Ser Asp Gln Ser Val Ala
    130                 135                 140

Gly Phe Asn Asp Glu Ala Ile Thr Ser Trp Leu Arg Phe Thr Trp Glu
145                 150                 155                 160

Ser Tyr Arg Ala Val Leu Asp Leu Leu Arg Asn Asn Ala Leu Leu Glu
                165                 170                 175

Ile Thr Tyr Ser Gly Val Val Lys Lys Thr Met His Phe Cys Leu Lys
            180                 185                 190
```

```
Tyr Gln Arg Lys Asn Glu Phe Lys Arg Leu Ala Glu Met Leu Arg Gln
            195                 200                 205

His Leu Asp Ala Ala Asn Tyr Gln Gln Ser Lys Ser Gly Asn Asn Leu
        210                 215                 220

Val Asp Leu Ser Asp Ala Asp Thr Leu Gln Arg Tyr Leu Asp Gln Arg
225                 230                 235                 240

Phe Gln Gln Val Asp Val Ser Val Lys Leu Glu Leu Trp His Glu Ala
                245                 250                 255

Tyr Arg Ser Ile Glu Asp Val Phe His Leu Met Lys Ile Ser Lys Arg
            260                 265                 270

Ala Pro Lys Pro Ser Thr Leu Ala Asn Tyr Tyr Glu Asn Leu Val Lys
        275                 280                 285

Val Phe Phe Val Ser Gly Asp Pro Leu Leu His Thr Thr Ala Trp Lys
290                 295                 300

Lys Phe Tyr Lys Leu Tyr Ser Thr Asn Pro Arg Ala Thr Glu Glu Glu
305                 310                 315                 320

Phe Lys Thr Tyr Ser Ser Thr Ile Phe Leu Ser Ala Ile Ser Thr Gln
                325                 330                 335

Leu Asp Glu Ile Pro Ser Ile Gly Tyr Asp Pro His Leu Arg Met Tyr
            340                 345                 350

Arg Leu Leu Asn Leu Asp Ala Lys Pro Thr Arg Lys Glu Met Leu Gln
        355                 360                 365

Ser Ile Ile Glu Asp Glu Ser Ile Tyr Gly Lys Val Asp Glu Glu Leu
        370                 375                 380

Lys Glu Leu Tyr Asp Ile Ile Glu Val Asn Phe Asp Val Asp Thr Val
385                 390                 395                 400

Lys Gln Gln Leu Glu Asn Leu Leu Val Lys Leu Ser Ser Lys Thr Tyr
                405                 410                 415

Phe Ser Gln Tyr Ile Ala Pro Leu Arg Asp Val Ile Met Arg Arg Val
            420                 425                 430

Phe Val Ala Ala Ser Gln Lys Phe Thr Thr Val Ser Gln Ser Glu Leu
        435                 440                 445

Tyr Lys Leu Ala Thr Leu Pro Ala Pro Leu Asp Leu Ser Ala Trp Asp
        450                 455                 460

Ile Glu Lys Ser Leu Leu Gln Ala Ala Val Glu Asp Tyr Val Ser Ile
465                 470                 475                 480

Thr Ile Asp His Glu Ser Ala Lys Val Thr Phe Ala Lys Asp Pro Phe
                485                 490                 495

Asp Ile Phe Ala Ser Thr Ala Ser Lys Glu Val Ser Glu Glu Glu Asn
            500                 505                 510

Thr Glu Pro Glu Val Gln Glu Glu Lys Glu Glu Thr Asp Glu Ala Leu
        515                 520                 525

Gly Pro Gln Glu Thr Glu Asp Gly Glu Glu Lys Glu Glu Glu Ser Asp
        530                 535                 540

Pro Val Ile Ile Arg Asn Ser Tyr Ile His Asn Lys Leu Leu Glu Leu
545                 550                 555                 560

Ser Asn Val Leu His Asp Val Asp Ser Phe Asn Asn Ala Ser Tyr Met
                565                 570                 575

Glu Lys Val Arg Ile Ala Arg Glu Thr Leu Ile Lys Lys Asn Lys Asp
            580                 585                 590

Asp Leu Glu Lys Ile Ser Lys Ile Val Asp Glu Arg Val Lys Arg Ser
        595                 600                 605
```

```
Gln Glu Gln Lys Gln Lys His Met Glu His Ala Ala Leu His Ala Glu
        610                 615                 620
Gln Asp Ala Glu Val Arg Gln Gln Arg Ile Leu Glu Glu Lys Ala Ala
625                 630                 635                 640
Ile Glu Ala Lys Leu Glu Glu Ala His Arg Arg Leu Ile Glu Lys
                645                 650                 655
Lys Lys Arg Glu Phe Glu Ala Ile Lys Glu Arg Glu Ile Thr Lys Met
            660                 665                 670
Ile Thr Glu Val Asn Ala Lys Gly His Val Tyr Ile Asp Pro Asn Glu
        675                 680                 685
Ala Lys Ser Leu Asp Leu Asp Thr Ile Lys Gln Val Ile Ala Glu
    690                 695                 700
Val Ser Lys Asn Lys Ser Glu Leu Glu Ser Arg Met Glu Tyr Ala Met
705                 710                 715                 720
Lys Lys Leu Asp His Thr Glu Arg Ala Leu Arg Lys Val Glu Leu Pro
                725                 730                 735
Leu Leu Gln Lys Glu Val Asp Lys Leu Gln Glu Thr Asp Thr Ala Asn
            740                 745                 750
Tyr Glu Ala Met Lys Lys Ile Val Asp Ala Ala Lys Ala Glu Tyr
        755                 760                 765
Glu Ala Arg Met Ala Asp Arg Lys Asn Leu Val Met Val Tyr Asp Asp
    770                 775                 780
Tyr Leu Lys Phe Lys Glu His Val Ser Gly Thr Lys Glu Ser Glu Leu
785                 790                 795                 800
Ala Ala Ile Arg Asn Gln Lys Lys Ala Glu Leu Glu Ala Ala Lys Lys
                805                 810                 815
Ala Arg Ile Glu Glu Val Arg Lys Arg Arg Tyr Glu Glu Ala Ile Ala
            820                 825                 830
Arg Arg Lys Glu Glu Ile Ala Asn Ala Glu Arg Gln Lys Arg Ala Gln
        835                 840                 845
Glu Leu Ala Glu Ala Thr Arg Lys Gln Arg Glu Ile Glu Glu Ala Ala
    850                 855                 860
Ala Lys Lys Ser Thr Pro Tyr Ser Phe Arg Ala Gly Asn Arg Glu Pro
865                 870                 875                 880
Pro Ser Thr Pro Ser Thr Leu Pro Lys Ala Thr Val Ser Pro Asp Lys
                885                 890                 895
Ala Lys Leu Asp Met Ile Ala Gln Lys Gln Arg Glu Met Glu Glu Ala
            900                 905                 910
Ile Glu Gln Arg Leu Ala Gly Arg Thr Ala Gly Ser Ser Pro Ala
        915                 920                 925
Thr Pro Ala Thr Pro Ala Thr Pro Ala Thr Pro Thr Pro Ser Ser Gly
    930                 935                 940
Pro Lys Lys Met Thr Met Ala Glu Lys Leu Arg Ala Lys Arg Leu Ala
945                 950                 955                 960
Lys Gly Gly Arg

<210> SEQ ID NO 6
<211> LENGTH: 958
<212> TYPE: PRT
<213> ORGANISM: Nicotiana sp.
<220> FEATURE:
<223> OTHER INFORMATION: peptide

<400> SEQUENCE: 6

Met Ala Thr Phe Ala Lys Pro Glu Asn Ala Leu Lys Arg Ala Glu Glu
```

```
  1               5                  10                 15
Leu Ile Thr Val Gly Gln Lys Gln Glu Ala Leu Gln Ala Leu His Asp
             20                 25              30
Leu Ile Thr Ser Arg Arg Tyr Arg Ala Trp Gln Lys Thr Leu Glu Arg
             35                 40              45
Ile Met Phe Lys Tyr Val Glu Leu Cys Val Asp Met Arg Arg Gly Arg
             50                 55              60
Phe Ala Lys Asp Gly Leu Ile Gln Tyr Arg Ile Val Cys Gln Gln Val
 65                  70                 75                   80
Asn Ile Asn Ser Leu Glu Glu Val Ile Lys His Phe Met His Leu Ala
                 85                 90              95
Thr Glu Arg Ala Glu Leu Ala Arg Asn Gln Ala Gln Ala Leu Glu Glu
             100                105             110
Ala Leu Asp Val Glu Asp Leu Glu Ala Asp Lys Arg Pro Glu Asp Leu
             115                120             125
Met Leu Ser Tyr Val Ser Gly Glu Lys Gly Lys Asp Arg Ser Asp Arg
             130                135             140
Glu Leu Val Thr Pro Trp Phe Lys Phe Leu Trp Glu Thr Tyr Arg Thr
145              150                155                   160
Val Leu Glu Ile Leu Arg Asn Asn Ser Arg Leu Glu Ala Leu Tyr Ala
                 165                170             175
Met Thr Ala His Arg Ala Phe Gln Phe Cys Lys Gln Tyr Lys Arg Thr
             180                185             190
Thr Glu Phe Arg Arg Leu Cys Glu Ile Ile Arg Asn His Leu Ala Asn
             195                200             205
Leu Asn Lys Tyr Arg Asp Gln Arg Asp Arg Pro Asp Leu Ser Ala Pro
210              215                220
Glu Ser Leu Gln Leu Tyr Leu Asp Thr Arg Phe Glu Gln Leu Lys Val
225              230                235                   240
Ala Thr Glu Leu Gly Leu Trp Gln Glu Ala Phe Arg Ser Ile Glu Asp
                 245                250             255
Ile Tyr Gly Leu Met Cys Met Val Lys Lys Thr Pro Lys Ala Ser Leu
                 260                265             270
Met Val Val Tyr Tyr Gly Lys Leu Thr Glu Ile Phe Trp Met Ser Ser
                 275                280             285
Asn His Leu Tyr His Ala Tyr Ala Trp Leu Lys Leu Phe Ser Leu Gln
290              295                300
Lys Ser Phe Asn Lys Asn Leu Ser Gln Lys Asp Leu Gln Leu Ile Ala
305              310                315                   320
Ser Ser Val Val Leu Ala Ala Leu Ser Val Pro Pro Tyr Asp Gln Ser
                 325                330             335
Tyr Gly Ala Ser His Leu Glu Leu Glu Asn Glu Lys Glu Arg Ser Leu
                 340                345             350
Arg Val Ala Asn Leu Ile Gly Phe Glu Val Glu Pro Lys Ala Glu Asn
                 355                360             365
Arg Val Ala Leu Ser Arg Ser Ser Leu Leu Ser Glu Leu Val Ser Lys
             370                375             380
Gly Val Met Ser Cys Val Thr Gln Glu Val Lys Asp Leu Tyr His Leu
385              390                395                   400
Leu Glu Asn Glu Phe Leu Pro Leu Asp Leu Ala Leu Lys Val Gln Pro
                 405                410             415
Val Leu Ser Lys Ile Ser Lys Leu Gly Gly Lys Leu Ser Ser Val Ser
                 420                425             430
```

-continued

```
Ser Val Pro Glu Val Gln Leu Ser Gln Tyr Val Pro Ala Leu Glu Lys
        435                 440                 445

Leu Ala Thr Leu Arg Leu Leu Gln Gln Val Ser Gln Val Tyr Gln Thr
        450                 455                 460

Ile Gln Ile Asp Asn Ile Ser Lys Met Ile Pro Phe Phe Asp Phe Thr
465                 470                 475                 480

Val Ile Glu Lys Ile Ser Val Asp Ala Val Arg Arg Asn Phe Leu Ala
                485                 490                 495

Ile Lys Val Asp His Met Lys Gly Leu Ser Ser Leu Val Asn Arg Val
                500                 505                 510

Leu Arg Arg Lys Asp Ser Gly Ile Ile Cys Leu Phe Leu Ala Glu Ser
        515                 520                 525

Leu Ser Lys Ala Arg Thr Met Ile Tyr Pro Pro Ala Lys Lys Ala Ala
        530                 535                 540

Lys Leu Gly Glu Ala Leu Ser Asn Leu Ala Glu Ile Val Glu Lys Glu
545                 550                 555                 560

His Lys Arg Leu Leu Ala Arg Lys Ser Ile Ile Glu Lys Arg Lys Glu
                565                 570                 575

Glu Gln Glu Arg Leu Leu Leu Glu Met Glu Arg Val Glu Glu Thr Lys
        580                 585                 590

Arg Arg Asp Val Gln Lys Met Thr Glu Glu Ala Glu Gln Lys Arg Ile
        595                 600                 605

Ala Ala Glu Tyr Glu Gln Arg Arg Asn Gln Arg Ile Leu Lys Glu Ile
        610                 615                 620

Glu Asp Arg Glu Leu Glu Glu Ala Gln Ala Leu Leu His Glu Ala Glu
625                 630                 635                 640

Lys Arg Ser Lys Arg Lys Lys Pro Val Leu Glu Gly Glu Lys Met
                645                 650                 655

Thr Lys Lys Val Ile Met Glu Leu Ala Leu Asn Glu Gln Leu Arg Glu
                660                 665                 670

Arg Gln Glu Met Glu Lys Lys Leu Leu Lys Phe Ala Lys Ser Met Asp
        675                 680                 685

His Leu Glu Arg Ala Lys Arg Glu Glu Ala Ala Pro Leu Ile Glu Ser
        690                 695                 700

Ala Phe Lys Gln Arg Leu Ala Glu Glu Ala Ala Leu His Glu Arg Glu
705                 710                 715                 720

Gln Gln Gln Glu Ile Glu Leu Ser Arg Gln Arg His Ala Gly Asp Leu
                725                 730                 735

Glu Glu Lys Arg Arg Leu Ala Arg Met Leu Glu Asn Lys Arg Ile Leu
        740                 745                 750

Gln Glu Lys Val Val Ser Ser Arg Glu Ala Glu Phe Thr Arg Met Lys
        755                 760                 765

Arg Glu Arg Gln Glu Arg Ile Ser Gln Ile Ile Gln Ser Arg Lys Gln
        770                 775                 780

Glu Arg Glu Ala Arg Arg Lys Met Ile Phe Phe Leu Arg Ser Glu Glu
785                 790                 795                 800

Glu Arg Gln Lys Arg Leu Gln Glu Glu Glu Ala Arg Lys Arg Glu
                805                 810                 815

Glu Ala Glu Arg Arg Lys Lys Glu Glu Ala Glu Arg Gln Ala Lys Leu
        820                 825                 830

Asp Glu Ile Ala Glu Lys Gln Arg Arg Met Leu Glu Leu Glu Glu
        835                 840                 845
```

```
Lys Glu Lys Arg Glu Arg Glu Ile Leu Arg Lys Ser Thr Ala Val
850                 855                 860

Leu Pro Lys Pro Ala Glu Pro Pro Thr Leu Gly Arg Pro Ala Glu Leu
865                 870                 875                 880

Gly Gly Ala Ala Pro Ile Pro Ala Ala Ala Thr Ala Pro Thr Pro
                885                 890                 895

Gly Pro Gly Lys Tyr Val Pro Lys His Leu Arg Thr Lys Met Asp Gly
            900                 905                 910

Ala Gly Gln Ala Pro Pro Glu Thr Asp Lys Trp Gly Gly Gly Ser
            915                 920                 925

Lys Pro Asp Asp Arg Pro Ser Trp Arg Asp Glu Arg Lys Pro Pro Ser
930                 935                 940

Phe Gly Ser Gly Ser Arg Thr Ser Trp Pro Ala Ser Arg Arg
945                 950                 955

<210> SEQ ID NO 7
<211> LENGTH: 1076
<212> TYPE: PRT
<213> ORGANISM: Caenorhabditis elegans

<400> SEQUENCE: 7

Met Ala Pro Asn Tyr Phe Gln Lys Pro Glu Ala Ala Leu Lys Arg Ala
1               5                   10                  15

Glu Glu Leu Ile Gln Val Gly Lys Glu Ser Asp Ala Leu Asp Thr Leu
            20                  25                  30

His Asp Thr Ile Lys Ala Arg Arg His Lys Gln Trp Thr Thr Val His
        35                  40                  45

Glu Gln Ile Met Ile Lys His Met Glu Leu Cys Val Asp Leu Lys Lys
    50                  55                  60

Gln His Leu Ala Lys Asp Ala Leu Phe Gln Tyr Lys Ala Leu Thr Gln
65                  70                  75                  80

Gln Ile Asn Val Lys Ser Leu Glu Thr Val Val His Phe Leu Lys
                85                  90                  95

Leu Ala Glu Gln Arg Thr Glu Asp Ala Gln Lys Gln Ser Ile Glu Lys
            100                 105                 110

Val Glu Glu Ile Gly Asp Leu Asp Gln Gly Asp Val Pro Glu Arg Leu
        115                 120                 125

Leu Leu Ala Val Val Ser Gly Ala Ala Ala Gln Asp Arg Met Asp Arg
130                 135                 140

Thr Val Leu Ala Pro Trp Leu Arg Phe Leu Trp Asp Ser Tyr Arg Asn
145                 150                 155                 160

Cys Leu Glu Leu Leu Arg Asn Asn Ala Gln Val Glu Gln Leu Tyr His
                165                 170                 175

Thr Ile Ser Arg His Ser Phe Thr Phe Cys Leu Arg Tyr Gln Arg Arg
            180                 185                 190

Thr Glu Phe Arg Lys Leu Cys Asp Leu Leu Arg Met His Leu Asn Gln
        195                 200                 205

Ile Gln Lys His Gln Tyr Ala Pro Asn Val Asn Ser Phe Arg Val Lys
    210                 215                 220

Leu Thr Ser Pro Glu Ser Leu Gly Leu Met Gln Asp Thr Arg Leu Ile
225                 230                 235                 240

Gln Leu Asp Thr Ala Ile Gln Met Glu Leu Trp Gln Glu Ala Tyr Lys
                245                 250                 255

Ser Ala Glu Asp Val His Gly Met Met Gln Leu Ser Lys Asp Lys Asp
            260                 265                 270
```

-continued

```
Lys Arg Thr Val Lys Pro Ala Ser Tyr Val Asn Tyr Tyr Asp Lys Leu
        275                 280                 285
Ala Leu Val Phe Trp Lys Ala Gly Asn Ser Leu Phe His Ala Ala Ala
290                 295                 300
Leu Leu Gln Lys Phe Ile Ile Tyr Lys Asp Met Lys Lys Ser Phe Thr
305                 310                 315                 320
Gln Asp Glu Ala Gln Glu Gln Ala Thr Arg Val Leu Leu Ala Thr Leu
                325                 330                 335
Ser Ile Pro Glu Gly Ser Asp Ser Pro Ser Asp Leu Ser Arg Asn Leu
                340                 345                 350
Asp Ile Glu Asp Gln His Val Ala Asn Met Arg Leu Leu Ser Asn Leu
                355                 360                 365
Leu Arg Leu Pro Ile Ala Pro Thr Lys Asn Gly Ile Leu Lys Glu Ala
370                 375                 380
Ala Arg Ile Gly Val Pro Glu Ala Ala Gly Gln Thr Ala Lys Asp Leu
385                 390                 395                 400
Tyr Lys Leu Leu Glu Ser Asn Phe Ser Pro Leu Lys Val Ala Lys Asp
                405                 410                 415
Val Gln Ser Val Leu Asp Thr Val Thr Arg Pro Asp His Leu Gln Tyr
                420                 425                 430
Val Glu Ser Leu Gln Ala Val Ala Ala Val Lys Ala Leu Lys Gln Val
                435                 440                 445
Ser Val Ile Tyr Glu Ala Ile Ser Trp Glu Arg Ile Arg Lys Ile Ile
                450                 455                 460
Pro Phe Tyr Ser Asp Leu Ala Leu Glu Arg Leu Val Glu Ala Ser
465                 470                 475                 480
Lys His Arg Ile Val Lys Ala Gln Leu Asp His Arg Ala Asp Cys Val
                485                 490                 495
Arg Phe Gly Ser Ser Asp Ala Thr Leu Ala Gly Gly Val Asp Glu Cys
                500                 505                 510
Asp Asn Asn Glu Gly Phe Thr Gly Asp Asp Thr Gln Leu Gly Val Glu
                515                 520                 525
Gly Val Arg Asn His Leu Glu Ala Met Tyr Thr Arg Leu Arg Gly Leu
530                 535                 540
Val Glu Gly Leu Asp Ala Glu Lys Arg Arg Lys Glu Ile Leu Lys Lys
545                 550                 555                 560
Ile Glu Gly Gln Val Thr Ser Tyr Glu Lys Asn Arg Pro Thr Glu Ile
                565                 570                 575
Glu Arg Ile His Arg Arg Lys Met Leu Glu Asn Tyr Lys Glu Asn
                580                 585                 590
Trp Glu Arg Val Lys Ala Glu Lys Thr Ala Ala Ala Thr Glu Gln
                595                 600                 605
Ala Lys Arg Glu Glu Ala Ala Arg Ala Glu Glu Met Lys Arg Leu Asp
                610                 615                 620
Glu Gln Asn Lys Glu Ser Glu Arg Lys Arg Lys Gln Ala Glu Gln Asp
625                 630                 635                 640
Glu Ile Gln Lys Lys Ile Lys Gln Asp Gln Leu Tyr Lys Met Gln Gln
                645                 650                 655
Asn Ala Ile Tyr Gln Glu Ile Ile Lys Glu Lys Gly Leu Glu Gln Phe
                660                 665                 670
Arg Asp Met Asp Pro Glu Gln Val Leu Arg Glu Gln Arg Glu Arg Leu
675                 680                 685
```

-continued

```
Asp Lys Glu Arg Ala Glu Thr Gln Arg Arg Leu Gln Gln Gln Glu Lys
    690                 695                 700
Asn Phe Asp His His Val Arg Ala Leu His Leu Glu Glu Leu Asn Glu
705                 710                 715                 720
Arg Arg Ala Val Met Asn Met Arg Leu Ser Glu Ala Pro Lys Leu His
                725                 730                 735
Asp Leu Tyr Glu Glu Ala Arg Ile Ala Lys Glu Ile Ala Ala His Asp
            740                 745                 750
Ser His Val Lys Leu Trp Gly Met Trp Asp Gln Val Arg Asp Ala Thr
        755                 760                 765
Phe Asp Trp Val Glu Ser Val Lys Ile Asp Asn Gln Glu Thr Leu Glu
    770                 775                 780
Lys Lys Leu Ser Asp Trp Gln Ala Lys Leu Glu Ala Val Arg Asn Asn
785                 790                 795                 800
Arg Leu Ala Glu Arg Ala Glu Asp Arg Lys Lys Arg Lys Glu Asp
                805                 810                 815
Ala Ile Gln Ala Lys Ile Ala Glu Glu Arg Lys Lys Arg Glu Glu Glu
            820                 825                 830
Glu Arg Ala Arg Leu Gln Val Ile Glu Gly Gln Arg Arg Gln His Asn
        835                 840                 845
Asp Gly Arg Gly Arg Arg Glu Met Glu Asn Ser Val Ala Met Gln Asp
    850                 855                 860
Asn Asp Trp Arg Arg Asn Pro Pro Arg Glu Ser Leu Pro Pro Arg Glu
865                 870                 875                 880
Thr Arg Pro Met Arg Asp Gly Pro Thr Arg Glu Pro Arg Glu Phe Arg
                885                 890                 895
Gly Asp Arg Asp Arg Glu Pro Arg Glu Pro Phe Arg Glu Val Pro Ser
            900                 905                 910
Ser Lys Ala Asp Thr Asp Asn Ser Trp Arg Ser Ser Ala Gln Pro Thr
        915                 920                 925
Arg Lys Pro Asp Asp Arg Arg Ser Asp Glu Phe Arg Arg Asn Asp Asp
    930                 935                 940
Val Arg Arg Asn Asp Asp Val Arg Arg Asn Asp Pro Pro Arg Pro Ala
945                 950                 955                 960
Ser Lys Ala Asp Thr Gly Asp Lys Trp Glu Arg Gly Val Lys Pro Val
                965                 970                 975
Val Ser Pro Pro Lys Thr Asp Ala Pro Ser Val Ser Glu Pro Lys Ser
            980                 985                 990
Glu Gly Pro Lys Arg Phe Val Pro Pro His Leu Arg Asn Arg Gln Gly
        995                 1000                1005
Gly Gly Gly Ala Gly Gly Ser Glu Glu Gln Ser Ala Pro Ala Arg Ser
    1010                1015                1020
Gly Asn Ser Asn Val Thr Ser Pro Pro Asp Arg Ala Gln Gly Leu Arg
1025                1030                1035                1040
Gly Pro Pro Pro Thr Gly Arg Asn Ser Leu Pro Arg Arg Asp Gly Pro
                1045                1050                1055
Pro Pro Arg Ser Asn Asn Thr Gly Asn Thr Gly Asn Ala Asp Ser Gly
            1060                1065                1070
Ser Trp Arg Lys
        1075

<210> SEQ ID NO 8
<211> LENGTH: 5301
<212> TYPE: DNA
```

<213> ORGANISM: Homo sapiens
<220> FEATURE:
<221> NAME/KEY: mat_peptide
<222> LOCATION: (127)..(4272)

<400> SEQUENCE: 8

| | | | | | |
|---|---|---|---|---|---|
| ccggctgggc | gcgggcatct | gctggcgagg | cgcgtgggac | cttacgctgg | ttccccttcg | 60 |
| tctcctctcc | cggcccgggc | cactagagag | ttcgctgacg | ccgggtgagc | tgagcctgcc | 120 |
| gccaagatgc | cggcctattt | ccagaggccg | gaaaatgccc | tcaaacgcgc | caacgaattt | 180 |
| cttgaggttg | gcaaaaagca | gcctgctctg | gatgttcttt | atgatgttat | gaaaagtaaa | 240 |
| aaacatagaa | catggcaaaa | gatacacgaa | ccaattatgt | tgaaatactt | ggaactttgc | 300 |
| gtggatcttc | gcaagagcca | cttggcaaag | gaggggttat | accagtataa | gaacatttgt | 360 |
| caacaggtga | acataaaatc | tctggaggat | gttgttaggg | catatttgaa | aatggcagag | 420 |
| gaaaaaactg | aagctgctaa | agaagaatct | cagcagatgt | tcttagatat | agaggatcta | 480 |
| gataatattc | aaactcctga | gagtgttctc | ctaagtgctg | taagtggtga | agacactcag | 540 |
| gatcgtactc | acagattact | tttaactcca | tgggttaaat | tcctgtggga | gtcttacagg | 600 |
| cagtgtttgg | accttcttag | aaacaattct | agagtagagc | gcctgtacca | tgatattgcc | 660 |
| cagcaagctt | tcaaattctg | cctccaatac | acgcgtaagc | tgaattccg | taaactgtgt | 720 |
| gacaatttga | gaatgcactt | atcgcagatt | cagcgccacc | ataaccaaag | tacggcaatc | 780 |
| aatcttaata | atccagagag | ccagtccatg | catttggaaa | ccagacttgt | tcagctggac | 840 |
| agtgctatca | gcatggaatt | gtggcaggaa | gcattcaaag | ctgtggaaga | tattcacggg | 900 |
| ctattctcct | tgtctaaaaa | accacctaaa | cctcagttga | tggcaaatta | ctataacaaa | 960 |
| gtctcaactg | tgttttggaa | atctggaaat | gctcttttc | atgcatctac | actccatcgt | 1020 |
| ctttaccatc | tctctagaga | aatgagaaag | aatctcacac | aagacgagat | gcaaagaatg | 1080 |
| tctactagag | tccttttagc | cactctttcc | atccctatta | ctcctgagcg | tacggatatt | 1140 |
| gctcgacttc | tggatacgga | tggcattata | gttgaaaaac | agcgtcgcct | tgcaacacta | 1200 |
| ctaggtcttc | aagccccacc | gacacgaatt | ggccttatta | atgatatggt | cagatttaat | 1260 |
| gtactacaat | atgttgtccc | agaagtgaaa | gacctttaca | attggcttga | agtagaattt | 1320 |
| aacccattaa | aactctgtga | gcgagtcaca | aaggttctaa | attgggttag | ggaacaacct | 1380 |
| gaaaaggaac | cggaattgca | gcagtatgtg | ccacaactgc | aaaacaacac | catcctccac | 1440 |
| cttctgcagc | aggtgtcaca | gatttatcag | agcattgagt | tttctcgttt | gacttctttg | 1500 |
| gttccttttg | ttgatgcttt | ccaactggaa | cgggccatag | tagatgcagc | caggcattgc | 1560 |
| gacttgcagg | ttcgtattga | tcacacttct | cggaccctga | gttttggatc | tgatttgaat | 1620 |
| tatgctactc | gagaagatgc | tccgattggt | cctcatttgc | aaagcatgcc | ttcagagcag | 1680 |
| ataagaaacc | agctgacagc | catgtcctca | gtacttgcaa | aagcacttga | agtcattaaa | 1740 |
| ccagctcata | tactgcaaga | gaaagaagaa | cagcatcagt | tggctgccac | tgcataacctt | 1800 |
| aaaaattcac | gaaaagagca | ccagcggatc | ctggctcgcc | gccagacaat | tgaggagaga | 1860 |
| aaagagcgcc | ttgagagtct | gaatattcag | cgtgagaaag | aagaattgga | acagagggaa | 1920 |
| gctgaactcc | agaaagtgcg | gaaggctgag | gaagagaggc | tgcgccagga | agcaaaggag | 1980 |
| agagagaagg | agcgtatctt | acaggaacat | gaacaaatca | aaagaaaac | tgtccgagag | 2040 |
| cgtttggagc | agatcaagaa | aacagaactg | ggtgccaaag | cattcaaaga | tattgatatt | 2100 |
| gaagaccttg | aggaattgga | tccagatttt | atcatggcta | aacaggttga | acaactggag | 2160 |

```
aaagaaaaga aagaacttca agaacgccta aagaatcaag aaaagaagat tgactattt     2220 gaaagagcca aacgtttgga agaaattcct ttgataaaga gcgcttacga ggaacagaga     2280
attaaagaca tggatctgtg ggagcaacaa gaggaagaaa gaattactac aatgcagcta     2340
gaacgtgaaa aggctcttga acataagaat cgaatgtcac gaatgcttga agacagagat     2400
ttattcgtaa tgcgactcaa agctgcacgg cagtctgttt atgaggaaaa acttaaacag     2460
tttgaagagc gattagcaga agaaaggcat aatcgattgg aagaacggaa aaggcagcgt     2520
aaagaagaac gcaggataac atactataga gaaaagaag aggaggagca gagaagggca     2580
ggagaacaaa tgctacaaga gcgggaagag agagagcgcg ccgaacgagc aaaacgcgag     2640
gaagagctac gagagtatca ggagcgggtg aagaaattag aagaagtgga aaggaaaaaa     2700
cgccaaaggg agttggaaat tgaagaacga gaacggcgta gagaggaaga gagaagactt     2760
ggcgatagtt ccctttctag aaaggactct cgttggggag atagagattc agaaggcacc     2820
tggagaaaag gacctgaagc agattctgag tggagaagag gcccgccaga gaaggagtgg     2880
agacgtggag aagggcgaga tgaggacagg tctcatagaa gagatgaaga gcggccccgg     2940
cgtctggggg atgttgaaga tagagagccc tctcttagac cagacgatga tcggttccc     3000 cggcgtggca tggatgatga cagaggccct agacgtggtc ctgaggaaga taggttctct     3060
cgtcgtgggg cagacgatga ccggccttcc tggcgtaaca cagatgatga caggcctccc     3120
agacgaattg ccgatgaaga caggggaaac tggcgtcatg cggatgatga cagaccacct     3180
agacgaggac tggatgagga cagaggaagc tggcgaacag ctgatgagga cagaggacca     3240
agacgtggga tggatgatga ccgggggccg aggcgaggag gcgctgatga tgagcgatca     3300
tcctggcgta atgctgatga tgaccggggt cccaggcgag ggttggatga tgatcggggt     3360
cccaggcgag gcatggatga tgaccggggt cccaggcgag gcatggatga tgaccggggt     3420
cccaggcgag gcatggatga tgaccggggt cccaggcgag ggttggatga tgatcgagga     3480
ccttggagga acgccgatga tgacagaatt cccaggcgtg gtgcagagga tgacaggggc     3540
ccttggagaa acatggatga tgatcgcctt tcaagacgtg ctgatgatga tcggtttccc     3600
agacggggtg atgactcaag acctggtcct tggagaccat tagtcaagcc aggtggatgg     3660
agagagaaag aaaaagccag agaggagagc tgggtccac ctcgagaatc aaggccatca     3720
gaagaacgtg aatgggacag agaaaagaa agggacagag ataatcaaga tcgggaggag     3780
aatgacaagg accctgagag agaaagggac agagagagag atgtggatcg agaggatcgc     3840
ttcagaagac ctagggatga aggtggctgg agaagaggac cagctgagga atcttcaagc     3900
tggagagact caagtcgccg ggacgatagg gatagggatg accgtcgccg tgagagggat     3960
gaccggcgtg atctaagaga aagacgagat ctaagagacg acagggaccg aagaggacct     4020
ccactcagat cagaacgtga agaagtaagt tcttggagac gtgctgatga caggaaagat     4080
gaccgggtgg aagagcggga ccctcctcgt cgagttcctc ccccagctct ttcaagagac     4140
cgagaaagag accgagaccg agaaagagaa ggtgaaaaag agaaggcctc atggagagct     4200
gagaaagata gggaatctct ccgtcgtact aaaaatgaga ctgatgaaga tggatggacc     4260
acagtacgac gttaacccgg gcgcgtctca agataatgga tttaaactgg tgtcttaaat     4320
aggtttgatc acattcaagg attattatac ttgtgcttca accaatctaa attggattct     4380
ttaatgttgt ttcaccataa cacaaaaagc atgaacttgt attaatccta tataatagat     4440
tgatcatgca ccatatccac aggaggttgg aaaaaccatg ccatttctg gaatttaagg     4500 gtgttgcatt atttcatcaa tcatttgttg acaaaaaaga aaaactaaaa aataaattta     4560
```

-continued

```
aaatgtgaac cttcaggtat tgagtaacac ctttatcttg gtatagaact gatactttt       4620 tttgattttg aaatatctga taataatttg gaatgaagta aggtcctgtt aaaatatatt      4680
tgaagaccct ttaaagcagt gaatctgaaa caattttcac acccttaagt ggttgatacg      4740
tacctatttt aggtattttg aggtatttac cataaactaa atttagaaat ttttagatt       4800 cacttgaagt aaacattaca aacattggat acggtggggt tttctttaga ttttacttga      4860
gagaaggtga gtacaaagca atttgcagtt gttgtaatga caagattact gcgcaagtgt      4920
gaatccaaac agtatagctt ttaaatttta aagcatttgg taaattatcg ctgagttttt      4980
ttctgttgcc aatagcaaac tgcttttcca ttaatggaga attcatgcct ttcaagcatt      5040
ttaaatatga caatatttat aaatgtatgg tttggaggaa tcgtttaaat tctctttcct      5100
aattttcttt cttttgaaga tagattcttt caacaagtaa tttgtagtaa tgactgtgtt      5160
gacttcaatt ttggagcgca gtagctatgt taaagatgaa ctatttggtc tcattgaagc      5220
caacacagaa cttgctgctg tgttttttct tcagtgataa ataaaatact taccaaaaaa      5280
aaaaaaaaaa aaaaaaaaaa a                                                5301
```

<210> SEQ ID NO 9
<211> LENGTH: 1382
<212> TYPE: PRT
<213> ORGANISM: Homo sapiens

<400> SEQUENCE: 9

```
Met Pro Ala Tyr Phe Gln Arg Pro Glu Asn Ala Leu Lys Arg Ala Asn
 1               5                  10                  15

Glu Phe Leu Glu Val Gly Lys Lys Gln Pro Ala Leu Asp Val Leu Tyr
            20                  25                  30

Asp Val Met Lys Ser Lys Lys His Arg Thr Trp Gln Lys Ile His Glu
        35                  40                  45

Pro Ile Met Leu Lys Tyr Leu Glu Leu Cys Val Asp Leu Arg Lys Ser
    50                  55                  60

His Leu Ala Lys Glu Gly Leu Tyr Gln Tyr Lys Asn Ile Cys Gln Gln
65                  70                  75                  80

Val Asn Ile Lys Ser Leu Glu Asp Val Val Arg Ala Tyr Leu Lys Met
                85                  90                  95

Ala Glu Glu Lys Thr Glu Ala Ala Lys Glu Glu Ser Gln Gln Met Val
            100                 105                 110

Leu Asp Ile Glu Asp Leu Asp Asn Ile Gln Thr Pro Glu Ser Val Leu
        115                 120                 125

Leu Ser Ala Val Ser Gly Glu Asp Thr Gln Asp Arg Thr Asp Arg Leu
    130                 135                 140

Leu Leu Thr Pro Trp Val Lys Phe Leu Trp Glu Ser Tyr Arg Gln Cys
145                 150                 155                 160

Leu Asp Leu Leu Arg Asn Asn Ser Arg Val Glu Arg Leu Tyr His Asp
                165                 170                 175

Ile Ala Gln Gln Ala Phe Lys Phe Cys Leu Gln Tyr Thr Arg Lys Ala
            180                 185                 190

Glu Phe Arg Lys Leu Cys Asp Asn Leu Arg Met His Leu Ser Gln Ile
        195                 200                 205

Gln Arg His His Asn Gln Ser Thr Ala Ile Asn Leu Asn Asn Pro Glu
    210                 215                 220

Ser Gln Ser Met His Leu Glu Thr Arg Leu Val Gln Leu Asp Ser Ala
225                 230                 235                 240
```

```
Ile Ser Met Glu Leu Trp Gln Glu Ala Phe Lys Ala Val Glu Asp Ile
            245                 250                 255

His Gly Leu Phe Ser Leu Ser Lys Lys Pro Lys Pro Gln Leu Met
        260                 265                 270

Ala Asn Tyr Tyr Asn Lys Val Ser Thr Val Phe Trp Lys Ser Gly Asn
        275                 280                 285

Ala Leu Phe His Ala Ser Thr Leu His Arg Leu Tyr His Leu Ser Arg
        290                 295                 300

Glu Met Arg Lys Asn Leu Thr Gln Asp Glu Met Gln Arg Met Ser Thr
305                 310                 315                 320

Arg Val Leu Leu Ala Thr Leu Ser Ile Pro Ile Thr Pro Glu Arg Thr
                325                 330                 335

Asp Ile Ala Arg Leu Leu Asp Thr Asp Gly Ile Ile Val Glu Lys Gln
                340                 345                 350

Arg Arg Leu Ala Thr Leu Leu Gly Leu Gln Ala Pro Pro Thr Arg Ile
        355                 360                 365

Gly Leu Ile Asn Asp Met Val Arg Phe Asn Val Leu Gln Tyr Val Val
        370                 375                 380

Pro Glu Val Lys Asp Leu Tyr Asn Trp Leu Glu Val Glu Phe Asn Pro
385                 390                 395                 400

Leu Lys Leu Cys Glu Arg Val Thr Lys Val Leu Asn Trp Val Arg Glu
                405                 410                 415

Gln Pro Glu Lys Glu Pro Glu Leu Gln Gln Tyr Val Pro Gln Leu Gln
                420                 425                 430

Asn Asn Thr Ile Leu His Leu Leu Gln Gln Val Ser Gln Ile Tyr Gln
                435                 440                 445

Ser Ile Glu Phe Ser Arg Leu Thr Ser Leu Val Pro Phe Val Asp Ala
450                 455                 460

Phe Gln Leu Glu Arg Ala Ile Val Asp Ala Ala Arg His Cys Asp Leu
465                 470                 475                 480

Gln Val Arg Ile Asp His Thr Ser Arg Thr Leu Ser Phe Gly Ser Asp
                485                 490                 495

Leu Asn Tyr Ala Thr Arg Glu Asp Ala Pro Ile Gly Pro His Leu Gln
                500                 505                 510

Ser Met Pro Ser Glu Gln Ile Arg Asn Gln Leu Thr Ala Met Ser Ser
                515                 520                 525

Val Leu Ala Lys Ala Leu Glu Val Ile Lys Pro Ala His Ile Leu Gln
                530                 535                 540

Glu Lys Glu Glu Gln His Gln Leu Ala Ala Thr Ala Tyr Leu Lys Asn
545                 550                 555                 560

Ser Arg Lys Glu His Gln Arg Ile Leu Ala Arg Arg Gln Thr Ile Glu
                565                 570                 575

Glu Arg Lys Glu Arg Leu Glu Ser Leu Asn Ile Gln Arg Glu Lys Glu
                580                 585                 590

Glu Leu Glu Gln Arg Glu Ala Glu Leu Gln Lys Val Arg Lys Ala Glu
                595                 600                 605

Glu Glu Arg Leu Arg Gln Glu Ala Lys Glu Arg Glu Lys Glu Arg Ile
                610                 615                 620

Leu Gln Glu His Glu Gln Ile Lys Lys Lys Thr Val Arg Glu Arg Leu
625                 630                 635                 640

Glu Gln Ile Lys Lys Thr Glu Leu Gly Ala Lys Ala Phe Lys Asp Ile
                645                 650                 655
```

```
Asp Ile Glu Asp Leu Glu Glu Leu Asp Pro Asp Phe Ile Met Ala Lys
            660                 665                 670
Gln Val Glu Gln Leu Glu Lys Glu Lys Lys Glu Leu Gln Glu Arg Leu
            675                 680                 685
Lys Asn Gln Glu Lys Lys Ile Asp Tyr Phe Glu Arg Ala Lys Arg Leu
            690                 695                 700
Glu Glu Ile Pro Leu Ile Lys Ser Ala Tyr Glu Glu Gln Arg Ile Lys
705                 710                 715                 720
Asp Met Asp Leu Trp Glu Gln Gln Glu Glu Arg Ile Thr Thr Met
                    725                 730                 735
Gln Leu Glu Arg Glu Lys Ala Leu Glu His Lys Asn Arg Met Ser Arg
            740                 745                 750
Met Leu Glu Asp Arg Asp Leu Phe Val Met Arg Leu Lys Ala Ala Arg
            755                 760                 765
Gln Ser Val Tyr Glu Gly Lys Leu Lys Gln Phe Glu Glu Arg Leu Ala
            770                 775                 780
Glu Glu Arg His Asn Arg Leu Glu Glu Arg Lys Arg Gln Arg Lys Glu
            785                 790                 795                 800
Glu Arg Arg Ile Thr Tyr Tyr Arg Glu Lys Glu Glu Glu Gln Arg
            805                 810                 815
Arg Ala Gly Glu Gln Met Leu Gln Glu Arg Glu Arg Glu Arg Ala
            820                 825                 830
Glu Arg Ala Lys Arg Glu Glu Leu Arg Glu Tyr Gln Glu Arg Val
            835                 840                 845
Lys Lys Leu Glu Glu Val Glu Arg Lys Lys Arg Gln Arg Glu Leu Glu
850                 855                 860
Ile Glu Glu Arg Glu Arg Arg Glu Glu Arg Arg Leu Gly Asp
865                 870                 875                 880
Ser Ser Leu Ser Arg Lys Asp Ser Arg Trp Gly Asp Arg Asp Ser Glu
            885                 890                 895
Gly Thr Trp Arg Lys Gly Pro Glu Ala Asp Ser Glu Trp Arg Arg Gly
            900                 905                 910
Pro Pro Glu Lys Glu Trp Arg Arg Gly Glu Gly Arg Asp Glu Asp Arg
            915                 920                 925
Ser His Arg Arg Asp Glu Glu Arg Pro Arg Arg Leu Gly Asp Val Glu
            930                 935                 940
Asp Arg Glu Pro Ser Leu Arg Pro Asp Asp Arg Val Pro Arg Arg
945                 950                 955                 960
Gly Met Asp Asp Arg Gly Pro Arg Gly Pro Glu Glu Asp Arg
            965                 970                 975
Phe Ser Arg Arg Gly Ala Asp Asp Arg Pro Ser Trp Arg Asn Thr
            980                 985                 990
Asp Asp Asp Arg Pro Pro Arg Arg Ile Ala Asp Glu Asp Arg Gly Asn
            995                 1000                1005
Trp Arg His Ala Asp Asp Arg Pro Pro Arg Arg Gly Leu Asp Glu
            1010                1015                1020
Asp Arg Gly Ser Trp Arg Thr Ala Asp Glu Asp Arg Gly Pro Arg Arg
1025                1030                1035                1040
Gly Met Asp Asp Asp Arg Gly Pro Arg Gly Gly Ala Asp Asp Glu
            1045                1050                1055
Arg Ser Ser Trp Arg Asn Ala Asp Asp Arg Gly Pro Arg Arg Gly
            1060                1065                1070
Leu Asp Asp Asp Arg Gly Pro Arg Arg Gly Met Asp Asp Asp Arg Gly
```

-continued

```
                1075                1080                1085
Pro Arg Arg Gly Met Asp Asp Asp Arg Gly Pro Arg Arg Gly Met Asp
    1090                1095                1100
Asp Asp Arg Gly Pro Arg Arg Gly Leu Asp Asp Arg Gly Pro Trp
1105                1110                1115                1120
Arg Asn Ala Asp Asp Arg Ile Pro Arg Arg Gly Ala Glu Asp Asp
            1125                1130                1135
Arg Gly Pro Trp Arg Asn Met Asp Asp Asp Arg Leu Ser Arg Arg Ala
        1140                1145                1150
Asp Asp Asp Arg Phe Pro Arg Arg Gly Asp Asp Ser Arg Pro Gly Pro
    1155                1160                1165
Trp Arg Pro Leu Val Lys Pro Gly Gly Trp Arg Glu Lys Glu Lys Ala
    1170                1175                1180
Arg Glu Glu Ser Trp Gly Pro Pro Arg Glu Ser Arg Pro Ser Glu Glu
1185                1190                1195                1200
Arg Glu Trp Asp Arg Glu Lys Glu Arg Asp Arg Asp Asn Gln Asp Arg
            1205                1210                1215
Glu Glu Asn Asp Lys Asp Pro Glu Arg Glu Arg Asp Arg Glu Arg Asp
            1220                1225                1230
Val Asp Arg Glu Asp Arg Phe Arg Arg Pro Arg Asp Glu Gly Gly Trp
        1235                1240                1245
Arg Arg Gly Pro Ala Glu Glu Ser Ser Ser Trp Arg Asp Ser Ser Arg
    1250                1255                1260
Arg Asp Asp Arg Asp Arg Asp Asp Arg Arg Arg Glu Arg Asp Asp Arg
1265                1270                1275                1280
Arg Asp Leu Arg Glu Arg Arg Asp Leu Arg Asp Asp Arg Asp Arg Arg
            1285                1290                1295
Gly Pro Pro Leu Arg Ser Glu Arg Glu Val Ser Ser Trp Arg Arg
        1300                1305                1310
Ala Asp Asp Arg Lys Asp Asp Arg Val Glu Glu Arg Asp Pro Pro Arg
        1315                1320                1325
Arg Val Pro Pro Pro Ala Leu Ser Arg Asp Arg Glu Arg Asp Arg Asp
    1330                1335                1340
Arg Glu Arg Glu Gly Glu Lys Glu Lys Ala Ser Trp Arg Ala Glu Lys
1345                1350                1355                1360
Asp Arg Glu Ser Leu Arg Arg Thr Lys Asn Glu Thr Asp Glu Asp Gly
            1365                1370                1375
Trp Thr Thr Val Arg Arg
        1380
```